United States Patent [19]

Jeschke et al.

[11] Patent Number: 5,624,897
[45] Date of Patent: Apr. 29, 1997

[54] CYCLIC DEPSIPEPTIDES HAVING 18 RING ATOMS, AND THEIR USE FOR COMBATING ENDOPARASITES

[75] Inventors: Peter Jeschke, Leverkusen; Jürgen Scherkenbeck, Wermelskirchen; Gerhard Bonse, Köln; Erwin Bischoff, Wuppertal; Norbert Mencke, Leverkusen; Achim Harder, Köln; Michael Londershausen, Erkrath; Hartwig Müller, Velbert, all of Germany

[73] Assignee: Bayer Aktiengesellschaft, Leverkusen, Germany

[21] Appl. No.: 353,409

[22] Filed: Dec. 9, 1994

[30] Foreign Application Priority Data

Dec. 16, 1993 [DE] Germany .......................... 43 42 907.6

[51] Int. Cl.$^6$ ........................... A61K 38/15; C07K 11/02
[52] U.S. Cl. ................................. 514/11; 530/323
[58] Field of Search ........................ 530/317, 323; 514/11, 450; 930/30, 270

[56] References Cited

U.S. PATENT DOCUMENTS 4,146,612  3/1979  Veber ......................... 514/11
4,794,117  12/1988  Corbiere ..................... 514/420

FOREIGN PATENT DOCUMENTS 4317458  12/1993  Germany .
9325543  12/1993  WIPO .

OTHER PUBLICATIONS

J. Antibiotics, vol. 45, No. 10, issued Oct. 1992, Tomoda et al, "Inhibition of Acyl-CoA: Cholesterol . . . ", pp. 1626–1632.
Biochemistry, vol. 23, issued 1984, Lifson et al, "Internal and External Alkali Ion Complexes . . . ", pp. 2577–2590.
Bioorg. Chem., vol. 1, No. 2, issued 1975, Pletneu et al, "Theoretical Conformational analysis . . . ", pp. 160–165.
J. Antibiotics, vol. 45, No. 8, issued Aug. 1992 Tomoda et al, "New Cyclodepsipeptides, Enniatins . . . ", pp. 1207–1215.
H.G. Lerchen & H. Kunz: Tetrahedron Lett. 26 (43) (1985), pp. 5257–5260.
H. Kunz & H.G. Lerchen Tetrahedron Lett. 28 (17) (1987), pp. 1873–1876.
B.F. Gisin: Helv. Chim. Acta 56 (1973), pp. 1476–1482.
R. Bowman et al. J. Chem. Soc. (1950), pp. 1346–1349.
J.R. McDermott et al. Can. J. Chem. 51 (1973), pp. 1915–1919.
H. Wurziger et al., Kontake [Catalysts] (Merck Darmstadt) 3 (1987), pp. 8–11 (cf. Abstract).
Fu et al., J. Amer. Chem. Soc. 76, (1954), pp. 6054–6058.
C.S. Rondestvedt et al. Org. Reactions 11 (1960), pp. 189–260.
U. Schmidt et al., Synthesis (1991), pp. 294–300;
Angew. Chem. 102 (1990), pp. 562–563.
Angew. Chem. 97 (1985), pp. 606–607.
J. Org. Chem. 47 (1982), pp. 3261–3264;
L.A. Blaise, Can. J. Chem. 70(5) (1992), pp. 1281–1287.
Chemical Abstracts 83 (13) abstract No. 114872(e) (1975).

*Primary Examiner*—Jeffrey E. Russel
*Attorney, Agent, or Firm*—Sprung Horn Kramer & Woods

[57] ABSTRACT

New cyclic depsipeptides having 18 ring atoms, of the general formula (I)

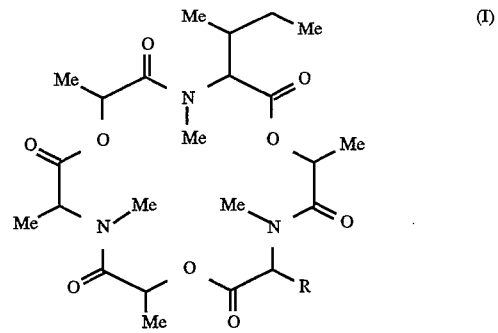

in which
  R represents hydrogen, straight-chain or branched or cyclic alkyl having up to 8 carbon atoms,
  and their optical isomers and racemates,
and their use for combating endoparasites in the field of medicine and veterinary medicine.

5 Claims, No Drawings

CYCLIC DEPSIPEPTIDES HAVING 18 RING ATOMS, AND THEIR USE FOR COMBATING ENDOPARASITES

The present invention relates to new cyclic depsipeptides having 18 ring atoms, to a process for their preparation, and to their use for combating endoparasites.

Certain cyclic depsipeptides having 18 ring atoms (enniatins) and processes for their preparation and their use as endoparasiticides are the subject-matter of an earlier, but not prior-published patent application (German Patent Application DE OS 317 458.2).

However, the activity of these previously known compounds is not entirely satisfactory at low application rates and low concentrations.

The present invention relates to:
1. New cyclic depsipeptides having 18 ring atoms, of the general formula (I)

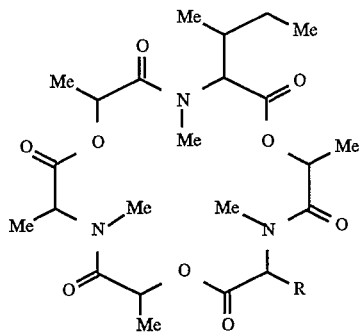

in which
R represents hydrogen, straight-chain or branched or cyclic alkyl having up to 8 carbon atoms and their optical isomers and racemates.

2. Process for the preparation of the new cyclic depsipeptides having 18 ring atoms, of the general formula (I)

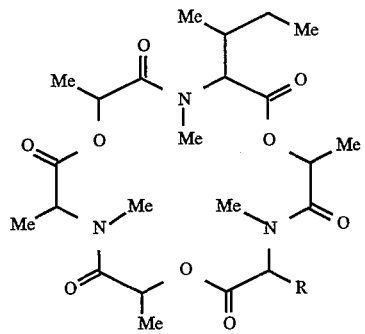

in which
R represents hydrogen, straight-chain or branched or cyclic alkyl having up to 8 carbon atoms and their optical isomers and racemates,
characterized in that open-chain hexadepsipeptides of the general formula (II)

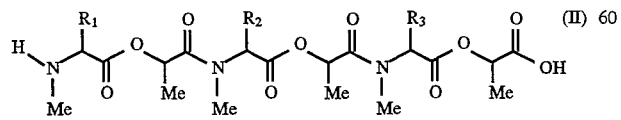

in which
one of the radicals $R^1$, $R^2$ and $R^3$ represents hydrogen, straight-chain or branched or cyclic alkyl having up to 8 carbon atoms and the two other radicals represent methyl and sec-butyl, are subjected to a cyclization reaction in the presence of a suitable coupling reagent, in the presence of a basic reaction auxiliary and in the presence of a diluent.

The new cyclic hexadepsipeptides of the general formula (I) add their optical isomers and racemates as well as their acid addition salts and metal salt complexes are outstandingly suitable for combating endoparasites, in particular in the field of medicine and veterinary medicine.

The preparation of the open-chain hexadepsipeptides of the formula (II) is described in an earlier, but not prior-published patent application (cf. German Patent Application P 4 317 458.2).

The compounds of the general formula (II)

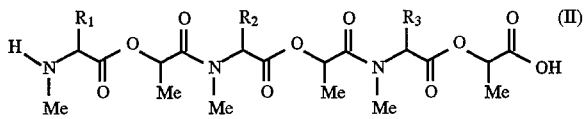

in which $R^1$, $R^2$ and $R^3$ have the meaning given further above, are obtained when, for example,
a) tetradepsipeptides of the general formula (III)

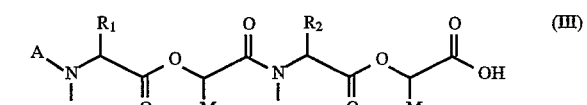

in which
A represents hydrogen or benzyl, or represents a group of the formula —CO—$R^4$, in which
$R^4$ represents straight-chain, branched alkoxy or aryloxy having up to 6 carbon atoms in the alkyl moiety,
$R^1$ and $R^2$ have the meaning given above,
are reacted, in a first reaction step, with didepsipeptides of the formula (VII)

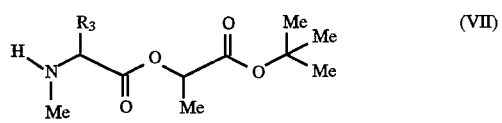

in which
$R^3$ has the meaning given further above, in the presence of suitable coupling reagents, in the presence of a basic reaction auxiliary and in the presence of a diluent, or
b) tetradepsipeptides of the general formula (IV)

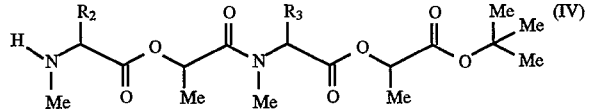

in which
$R^2$ and $R^3$ have the meaning given further above, are reacted, in a first reaction step, with depsipeptides of the general formula (V)

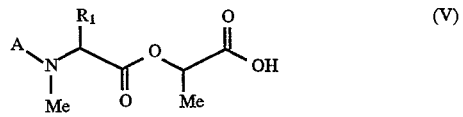

in which
A and $R^1$ have the meaning given further above, in the presence of suitable coupling reagents, in the presence of a basic reaction auxiliary and in the presence of a diluent, then, in a second reaction step, the open-chain hexadepsipeptides resulting from process a) or b), of the general formula

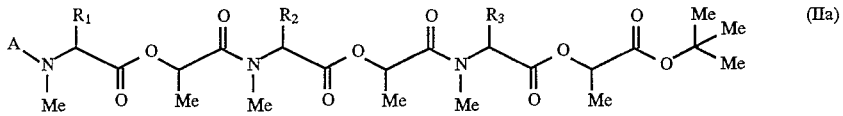

in which

A, R¹, R² and R³ have the meaning mentioned above, are subjected to C-terminal hydrolysis in the presence of a diluent and, if appropriate, in the presence of a protonic acid, or subjected to N-terminal deblocking in the presence of a diluent and, if appropriate, in the presence of a suitable catalyst, then, in a third reaction step, the resulting open-chain hexadepsipeptides of the general formula

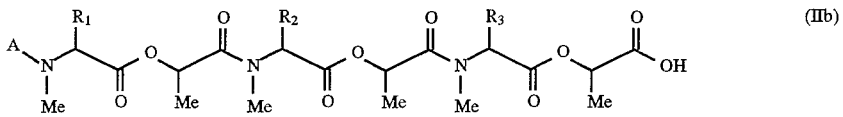

or

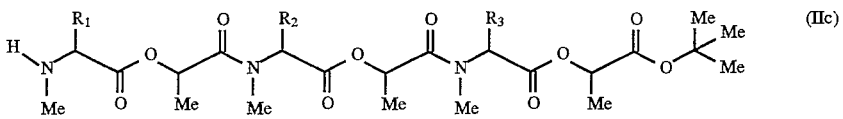

in which

A, R¹, R² and R³ have the abovementioned meaning, are subjected to N-terminal deblocking in the presence of a diluent and, if appropriate, in the presence of a suitable catalyst, or subjected to a further C-terminal hydrolysis step in the presence of a diluent and in the presence of a protonic acid.

Formula (I) provides a general definition of the cyclic depsipeptides having 18 ring atoms according to the invention.

Preferred compounds of the formula (I) are those, in which

R represents hydrogen, straight-chain or branched $C_{1-8}$-alkyl, in particular methyl, ethyl, propyl, isopropyl, butyl, isobutyl, sec-butyl, tert-butyl, pentyl, sec-pentyl, 1,2-dimethylpropyl, neopentyl, 1-ethylpropyl, 1,1-dimethylpropyl, hexyl, isohexyl, sec-hexyl, heptyl, isoheptyl, sec-heptyl, tert-heptyl, octyl, isooctyl, sec-octyl, $C_{3-7}$-cycloalkyl, in particular cyclopentyl, cyclohexyl, cycloheptyl, $C_{3-7}$-cycloalkyl-$C_{1-4}$-alkyl, in particular cyclopentylmethyl, cyclohexylmethyl or cycloheptylmethyl.

The compounds of the general formula (I) can have 6 to 8 centres of chirality.

The optically active compounds of the general formula (I) have at least one fixed configuration on one of the 6 to 8 centres of chirality which are possible, but there may be no fixed configuration on the remaining centres of chirality.

Particularly preferred compounds of the general formula (I) are those in which

R represents hydrogen, methyl, ethyl, propyl isopropyl, butyl, isobutyl or sec-butyl.

Very particularly preferred compounds of the general formula (I) are those in which R represents methyl, ethyl or sec-butyl, and whose stereoisomeric compounds have the meaning given below, cyclo(-N-methyl-L-alanyl-D-lactyl-N-methyl-D-isoleucyl-D-lactyl-N-methyl-L-alanyl-D-lactyl-), cyclo(-N-methyl-L-alanyl-D-lactyl-N-methyl-L-isoleucyl-D-lactyl-N-methyl-L-alanyl-D-lactyl-), cyclo(-N-methyl-L-alanyl-D-lactyl-N-methyl-L-alloisoleucyl-D-lactyl-N-methyl-L-alanyl-D-lactyl-), cyclo(-N-methyl-L-alanyl-D-lactyl-N-methyl-L-isoleucyl-L-lactyl-N-methyl-L-alanyl-D-lactyl-), cyclo(-N-methyl-L-alanyl-D-lactyl-N-methyl-D-isoleucyl-L-lactyl-N-methyl-L-alanyl-D-lactyl-), cyclo(-N-methyl-D-alanyl-L-lactyl-N-methyl-D-isoleucyl-D-lactyl-N-methyl-D-alanyl-L-lactyl-), cyclo(-N-methyl-D-alanyl-L-lactyl-N-methyl-L-isoleucyl-L-lactyl-N-methyl-D-alanyl-L-lactyl-), cyclo(-N-methyl-D-alanyl-L-lactyl-N-methyl-L-isoleucyl-D-lactyl-N-methyl-D-alanyl-L-lactyl-), cyclo(-N-methyl-D-alanyl-L-lactyl-N-methyl-D-isoleucyl-L-lactyl-N-methyl-D-alanyl-L-lactyl-), cyclo(-N-methyl-D-alanyl-L-lactyl-N-methyl-D-alloisoleucyl-L-lactyl-N-methyl-D-alanyl-L-lactyl-), cyclo(-N-methyl-L-alanyl-D-lactyl-N-methyl-D-isoleucyl-D-lactyl-N-methyl-L-2-aminobutyryl-D-lactyl-), cyclo(-N-methyl-L-alanyl-D-lactyl-N-methyl-L-isoleucyl-D-lactyl-N-methyl-L-2-aminobutyryl-D-lactyl-), cyclo(-N-methyl-L-alanyl-D-lactyl-N-methyl-L-alloisoleucyl-D-lactyl-N-methyl-L-2-aminobutyryl-D-lactyl-), cyclo(-N-methyl-L-alanyl-D-lactyl-N-methyl-D-isoleucyl-L-lactyl-N-methyl-L-2-aminobutyryl-D-lactyl-), cyclo(-N-methyl-L-alanyl-D-lactyl-N-methyl-L-isoleucyl-D-lactyl-N-methyl-L-2-aminobutyryl-D-lactyl-), cyclo(-N-methyl-D-alanyl-L-lactyl-N-methyl-D-isoleucyl-D-lactyl-N-methyl-D-2-aminobutyryl-L-lactyl-), cyclo(-N-methyl-D-alanyl-L-lactyl-N-methyl-L-isoleucyl-L-lactyl-N-methyl-D-2-aminobutyryl-L-lactyl-), cyclo(-N-methyl-D-alanyl-L-lactyl-N-methyl-L-isoleucyl-D-lactyl-N-methyl-D-2-aminobutyryl-L-lactyl-), cyclo(-N-methyl-D-alanyl-L-lactyl-N-methyl-D-isoleucyl-L-lactyl-N-methyl-D-2-aminobutyryl-L-lactyl-), cyclo(-N-methyl-D-alanyl-L-lactyl-N-methyl-D-alloisoleucyl-L-lactyl-N-methyl-D-2-aminobutyryl-L-lactyl-), cyclo(-N-methyl-L-alanyl-D-lactyl-N-methyl-D-isoleucyl-D-lactyl-N-methyl-L-isoleucyl-D-lactyl-), cyclo(-N-methyl-L-alanyl-D-lactyl-N-methyl-L-isoleucyl-D-lactyl-N-methyl-L-isoleucyl-D-lactyl-), cyclo(-N-methyl-L-alanyl-D-lactyl-N-methyl-L-alloisoleucyl-D-lactyl-N-methyl-L-isoleucyl-D-lactyl-),
cyclo(-N-methyl-L-alanyl-D-lactyl-N-methyl-L-isoleucyl-D-lactyl-N-methyl-L-alloisoleucyl-D-lactyl-),
cyclo(-N-methyl-L-alanyl-D-lactyl-N-methyl-L-alloisoleucyl-D-lactyl-N-methyl-L-alloisoleucyl-D-lactyl-),
cyclo(-N-methyl-L-alanyl-D-lactyl-N-methyl-L-isoleucyl-L-lactyl-N-methyl-L-isoleucyl-D-lactyl-),
cyclo(-N-methyl-L-alanyl-D-lactyl-N-methyl-D-isoleucyl-L-lactyl-N-methyl-L-isoleucyl-D-lactyl-),
cyclo(-N-methyl-D-alanyl-L-lactyl-N-methyl-D-isoleucyl-D-lactyl-N-methyl-D-isoleucyl-L-lactyl-),
cyclo(-N-methyl-D-alanyl-L-lactyl-N-methyl-L-isoleucyl-L-lactyl-N-methyl-D-isoleucyl-L-lactyl-),
cyclo(-N-methyl-D-alanyl-L-lactyl-N-methyl-L-isoleucyl-D-lactyl-N-methyl-D-isoleucyl-L-lactyl-),
cyclo(-N-methyl-D-alanyl-L-lactyl-N-methyl-D-isoleucyl-L-lactyl-N-methyl-D-isoleucyl-L-lactyl-),
cyclo(-N-methyl-D-alanyl-L-lactyl-N-methyl-D-alloisoleucyl-L-lactyl-N-methyl-D-isoleucyl-L-lactyl-),
cyclo(-N-methyl-D-alanyl-L-lactyl-N-methyl-D-isoleucyl-L-lactyl-N-methyl-D-alloisoleucyl-L-lactyl-),
cyclo(-N-methyl-D-alanyl-L-lactyl-N-methyl-D-alloisoleucyl-L-lactyl-N-methyl-D-alloisoleucyl-L-lactyl-).

The compounds of the general formula (I) can exist in optically active, stereoisomeric forms or in the form of racemic mixtures. However, optically active, stereoisomeric forms of the compounds of the general formula (I) are preferred.

The following stereoisomeric forms of the compounds of the general formula (I) may be mentioned individually:
cyclo(-N-methyl-L-alanyl-D-lactyl-N-methyl-D-isoleucyl-D-lactyl-N-methyl-glycyl-D-lactyl-),
cyclo(-N-methyl-L-alanyl-D-lactyl-N-methyl-L-isoleucyl-D-lactyl-N-methyl-glycyl-D-lactyl-),
cyclo(-N-methyl-L-alanyl-D-lactyl-N-methyl-L-alloisoleucyl-D-lactyl-N-methyl-glycyl-D-lactyl-),
cyclo(-N-methyl-L-alanyl-D-lactyl-N-methyl-L-isoleucyl-D-lactyl-N-methyl-glycyl-D-lactyl-),
cyclo(-N-methyl-L-alanyl-D-lactyl-N-methyl-D-isoleucyl-L-lactyl-N-methyl-glycyl-D-lactyl-),
cyclo(-N-methyl-D-alanyl-L-lactyl-N-methyl-D-isoleucyl-D lactyl-N-methyl-glycyl-L-lactyl-),
cyclo(-N-methyl-D-alanyl-L-lactyl-N-methyl-L-isoleucyl-L-lactyl-N-methyl-glycyl-L-lactyl-),
cyclo(-N-methyl-D-alanyl-L-lactyl-N-methyl-L-isoleucyl-D-lactyl-N-methyl-glycyl-L-lactyl-),
cyclo(-N-methyl-D-alanyl-L-lactyl-N-methyl-D-isoleucyl-L-lactyl-N-methyl-glycyl-L-lactyl-),
cyclo(-N-methyl-D-alanyl-L-lactyl-N-methyl-D-alloisoleucyl-L-lactyl-N-methyl-glycyl-L-lactyl-),
cyclo(-N-methyl-L-alanyl-D-lactyl-N-methyl-D-isoleucyl-D-lactyl-N-methyl-D-alanyl-D-lactyl-),
cyclo(-N-methyl-D-alanyl-L-lactyl-N-methyl-D-isoleucyl-D-lactyl-N-methyl-D-alanyl-D-lactyl-),
cyclo(-N-methyl-D-alanyl-D-lactyl-N-methyl-L-isoleucyl-D-lactyl-N-methyl-D-alanyl-D-lactyl-),
cyclo(-N-methyl-D-alanyl-D-lactyl-N-methyl-D-isoleucyl-L-lactyl-N-methyl-D-alanyl-D-lactyl-),
cyclo(-N-methyl-D-alanyl-D-lactyl-N-methyl-D-isoleucyl-D-lactyl-N-methyl-L-alanyl-D-lactyl-),
cyclo(-N-methyl-D-alanyl-D-lactyl-N-methyl-D-isoleucyl-D-lactyl-N-methyl-D-alanyl-L-lactyl-),
cyclo(-N-methyl-D-alanyl-D-lactyl-N-methyl-D-isoleucyl-D-lactyl-N-methyl-D-alanyl-D-lactyl-), cyclo(-N-methyl-D-alanyl-L-lactyl-N-methyl-L-isoleucyl-L-lactyl-N-methyl-L-alanyl-L-lactyl-),
cyclo(-N-methyl-L-alanyl-D-lactyl-N-methyl-L-isoleucyl-L-lactyl-N-methyl-L-alanyl-L-lactyl-),
cyclo(-N-methyl-L-alanyl-L-lactyl-N-methyl-D-isoleucyl-L-lactyl-N-methyl-L-alanyl-L-lactyl-),
cyclo(-N-methyl-L-alanyl-L-lactyl-N-methyl-L-isoleucyl-D-lactyl-N-methyl-L-alanyl-L-lactyl-),
cyclo(-N-methyl-L-alanyl-L-lactyl-N-methyl-L-isoleucyl-L-lactyl-N-methyl-D-alanyl-L-lactyl-),
cyclo(-N-methyl-L-alanyl-L-lactyl-N-methyl-L-isoleucyl-L-lactyl-N-methyl-L-alanyl-D-lactyl-),
cyclo(-N-methyl-L-alanyl-L-lactyl-N-methyl-L-isoleucyl-L-lactyl-N-methyl-L-alanyl-L-lactyl-),
cyclo(-N-methyl-L-alanyl-L-lactyl-N-methyl-D-isoleucyl-D-lactyl-N-methyl-D-alanyl-D-lactyl-),
cyclo(-N-methyl-L-alanyl-D-lactyl-N-methyl-L-isoleucyl-D-lactyl-N-methyl-D-alanyl-D-lactyl-),
cyclo(-N-methyl-L-alanyl-L-lactyl-N-methyl-D-isoleucyl-L-lactyl-N-methyl-D-alanyl-D-lactyl-),
cyclo(-N-methyl-L-alanyl-D-lactyl-N-methyl-D-isoleucyl-D-lactyl-N-methyl-D-alanyl-L-lactyl-),
cyclo(-N-methyl-D-alanyl-L-lactyl-N-methyl-D-isoleucyl-D-lactyl-N-methyl-D-alanyl-D-lactyl-),
cyclo(-N-methyl-D-alanyl-L-lactyl-N-methyl-D-isoleucyl-L-lactyl-N-methyl-D-alanyl-D-lactyl-),
cyclo(-N-methyl-D-alanyl-D-lactyl-N-methyl-L-isoleucyl-L-lactyl-N-methyl-D-alanyl-D-lactyl-),
cyclo(-N-methyl-D-alanyl-D-lactyl-N-methyl-L-isoleucyl-D-lactyl-N-methyl-L-alanyl-D-lactyl-),
cyclo(-N-methyl-D-alanyl-D-lactyl-N-methyl-D-isoleucyl-L-lactyl-N-methyl-L-alanyl-D-lactyl-),
cyclo(-N-methyl-D-alanyl-D-lactyl-N-methyl-D-isoleucyl-D-lactyl-N-methyl-L-alanyl-L-lactyl-),
cyclo(-N-methyl-D-alanyl-D-lactyl-N-methyl-D-isoleucyl-L-lactyl-N-methyl-L-alanyl-L-lactyl-),
cyclo(-N-methyl-D-alanyl-D-lactyl-N-methyl-D-isoleucyl-D-lactyl-N-methyl-L-alanyl-L-lactyl-),
cyclo(-N-methyl-D-alanyl-L-lactyl-N-methyl-D-isoleucyl-D-lactyl-N-methyl-L-alanyl-L-lactyl-),
cyclo(-N-methyl-D-alanyl-L-lactyl-N-methyl-D-isoleucyl-L-lactyl-N-methyl-L-alanyl-L-lactyl-),
cyclo(-N-methyl-D-alanyl-L-lactyl-N-methyl-L-isoleucyl-L-lactyl-N-methyl-L-alanyl-L-lactyl-),
cyclo(-N-methyl-D-alanyl-L-lactyl-N-methyl-L-isoleucyl-D-lactyl-N-methyl-L-alanyl-L-lactyl-),
cyclo(-N-methyl-D-alanyl-L-lactyl-N-methyl-L-isoleucyl-L-lactyl-N-methyl-L-alanyl-D-lactyl-),
cyclo(-N-methyl-L-alanyl-D-lactyl-N-methyl-L-isoleucyl-D-lactyl-N-methyl-L-alanyl-L-lactyl-),
cyclo(-N-methyl-L-alanyl-D-lactyl-N-methyl-L-isoleucyl-L-lactyl-N-methyl-D-alanyl-L-lactyl-),
cyclo(-N-methyl-L-alanyl-L-lactyl-N-methyl-D-isoleucyl-D-lactyl-N-methyl-L-alanyl-L-lactyl-),
cyclo(-N-methyl-L-alanyl-L-lactyl-N-methyl-D-isoleucyl-L-lactyl-N-methyl-D-alanyl-L-lactyl-),
cyclo(-N-methyl-L-alanyl-L-lactyl-N-methyl-D-isoleucyl-L-lactyl-N-methyl-L-alanyl-D-lactyl-),
cyclo(-N-methyl-L-alanyl-L-lactyl-N-methyl-L-isoleucyl-D-lactyl-N-methyl-D-alanyl-L-lactyl-),
cyclo(-N-methyl-L-alanyl-L-lactyl-N-methyl-L-isoleucyl-D-lactyl-N-methyl-L-alanyl-D-lactyl-),
cyclo(-N-methyl-L-alanyl-L-lactyl-N-methyl-L-isoleucyl-D-lactyl-N-methyl-D-alanyl-L-lactyl-),
cyclo(-N-methyl-L-alanyl-L-lactyl-N-methyl-L-isoleucyl-D-lactyl-N-methyl-D-alanyl-L-lactyl-),
cyclo(-N-methyl-L-alanyl-L-lactyl-N-methyl-L-isoleucyl-D-lactyl-N-methyl-D-alanyl-D-lactyl-),
cyclo(-N-methyl-L-alanyl-L-lactyl-N-methyl-L-isoleucyl-L-lactyl-N-methyl-D-alanyl-D-lactyl-), cyclo(-N-methyl-D-alanyl-L-lactyl-N-methyl-L-isoleucyl-
L-lactyl-N-methyl-D-alanyl-D-lactyl-),
cyclo(-N-methyl-D-alanyl-D-lactyl-N-methyl-L-isoleucyl-
L-lactyl-N-methyl-L-alanyl-D-lactyl-),
cyclo(-N-methyl-D-alanyl-D-lactyl-N-methyl-D-isoleucyl-
L-lactyl-N-methyl-L-alanyl-L-lactyl-),
cyclo(-N-methyl-L-alanyl-D-lactyl-N-methyl-L-isoleucyl-
L-lactyl-N-methyl-D-alanyl-D-lactyl-),
cyclo(-N-methyl-L-alanyl-D-lactyl-N-methyl-D-isoleucyl-
D-lactyl-N-methyl-L-alanyl-L-lactyl-),
cyclo(-N-methyl-L-alanyl-D-lactyl-N-methyl-L-isoleucyl-
D-lactyl-N-methyl-D-alanyl-L-lactyl-),
cyclo(-N-methyl-D-alanyl-L-lactyl-N-methyl-L-isoleucyl-
D-lactyl-N-methyl-L-alanyl-D-lactyl-),
cyclo(-N-methyl-D-alanyl-L-lactyl-N-methyl-D-isoleucyl-
L-lactyl-N-methyl-L-alanyl-D-lactyl-),
cyclo(-N-methyl-D-alanyl-L-lactyl-N-methyl-D-isoleucyl-
D-lactyl-N-methyl-L-alanyl-L-lactyl-),
cyclo(-N-methyl-D-alanyl-D-lactyl-N-methyl-L-isoleucyl-
L-lactyl-N-methyl-D-alanyl-L-lactyl-),
cyclo(-N-methyl-D-alanyl-D-lactyl-N-methyl-L-isoleucyl-
D-lactyl-N-methyl-L-alanyl-L-lactyl-),
cyclo(-N-methyl-L-alanyl-L-lactyl-N-methyl-D-isoleucyl-
D-lactyl-N-methyl-D-alanyl-L-lactyl-),
cyclo(-N-methyl-L-alanyl-D-lactyl-N-methyl-D-isoleucyl-
L-lactyl-N-methyl-D-alanyl-L-lactyl-),
cyclo(-N-methyl-L-alanyl-L-lactyl-N-methyl-D-isoleucyl-
D-lactyl-N-methyl-L-alanyl-D-lactyl-),
cyclo(-N-methyl-L-alanyl-L-lactyl-N-methyl-D-isoleucyl-
L-lactyl-N-methyl-D-alanyl-D-lactyl-),
cyclo(-N-methyl-L-alanyl-D-lactyl-N-methyl-D-isoleucyl-
D-lactyl-N-methyl-D-alanyl-D-lactyl-),
cyclo(-N-methyl-D-alanyl-L-lactyl-N-methyl-D-isoleucyl-
D-lactyl-N-methyl-D-2-aminobutyryl-D-lactyl-),
cyclo(-N-methyl-D-alanyl-D-lactyl-N-methyl-L-isoleucyl-
D-lactyl-N-methyl-D-2-aminobutyryl-D-lactyl-),
cyclo(-N-methyl-D-alanyl-D-lactyl-N-methyl-D-isoleucyl-
L-lactyl-N-methyl-D-2-aminobutyryl-D-lactyl-),
cyclo(-N-methyl-D-alanyl-D-lactyl-N-methyl-D-isoleucyl-
D-lactyl-N-methyl-L-2-aminobutyryl-D-lactyl-),
cyclo(-N-methyl-D-alanyl-D-lactyl-N-methyl-D-isoleucyl-
D-lactyl-N-methyl-D-2-aminobutyryl-L-lactyl-),
cyclo(-N-methyl-D-alanyl-D-lactyl-N-methyl-D-isoleucyl-
D-lactyl-N-methyl-D-2-aminobutyryl-D-lactyl-),
cyclo(-N-methyl-D-alanyl-L-lactyl-N-methyl-L-isoleucyl-
L-lactyl-N-methyl-L-2-aminobutyryl-L-lactyl-),
cyclo(-N-methyl-L-alanyl-L-lactyl-N-methyl-D-isoleucyl-
L-lactyl-N-methyl-L-2-aminobutyryl-L-lactyl-),
cyclo(-N-methyl-L-alanyl-L-lactyl-N-methyl-D-isoleucyl-
L-lactyl-N-methyl-L-2-aminobutyryl-L-lactyl-),
cyclo(-N-methyl-L-alanyl-L-lactyl-N-methyl-L-isoleucyl-
D-lactyl-N-methyl-L-2-aminobutyryl-L-lactyl-),
cyclo(-N-methyl-L-alanyl-L-lactyl-N-methyl-L-isoleucyl-
L-lactyl-N-methyl-D-2-aminobutyryl-L-lactyl-),
cyclo(-N-methyl-L-alanyl-L-lactyl-N-methyl-L-isoleucyl-
L-lactyl-N-methyl-L-2-aminobutyryl-D-lactyl-),
cyclo(-N-methyl-L-alanyl-L-lactyl-N-methyl-L-isoleucyl-
L-lactyl-N-methyl-L-2-aminobutyryl-L-lactyl-),
cyclo(-N-methyl-L-alanyl-L-lactyl-N-methyl-D-isoleucyl-
D-lactyl-N-methyl-D-2-aminobutyryl-D-lactyl-),
cyclo(-N-methyl-L-alanyl-D-lactyl-N-methyl-L-isoleucyl-
D-lactyl-N-methyl-D-2-aminobutyryl-D-lactyl-),
cyclo(-N-methyl-L-alanyl-D-lactyl-N-methyl-D-isoleucyl-
L-lactyl-N-methyl-D-2-aminobutyryl-D-lactyl-),
cyclo(-N-methyl-L-alanyl-D-lactyl-N-methyl-D-isoleucyl-
D-lactyl-N-methyl-L-2-aminobutyryl-D-lactyl-),
cyclo(-N-methyl-D-alanyl-L-lactyl-N-methyl-L-isoleucyl-
D-lactyl-N-methyl-D-2-aminobutyryl-D-lactyl-), cyclo(-N-methyl-D-alanyl-L-lactyl-N-methyl-D-isoleucyl-
L-lactyl-N-methyl-D-2-aminobutyryl-D-lactyl-),
cyclo(-N-methyl-D-alanyl-L-lactyl-N-methyl-D-isoleucyl-
D-lactyl-N-methyl-L-2-aminobutyryl-D-lactyl-),
cyclo(-N-methyl-D-alanyl-D-lactyl-N-methyl-L-isoleucyl-
L-lactyl-N-methyl-D-2-aminobutyryl-D-lactyl-),
cyclo(-N-methyl-D-alanyl-D-lactyl-N-methyl-L-isoleucyl-
D-lactyl-N-methyl-L-2-aminobutyryl-D-lactyl-),
cyclo(-N-methyl-D-alanyl-D-lactyl-N-methyl-L-isoleucyl-
D-lactyl-N-methyl-D-2-aminobutyryl-D-lactyl-),
cyclo(-N-methyl-D-alanyl-D-lactyl-N-methyl-D-isoleucyl-
L-lactyl-N-methyl-D-2-aminobutyryl-D-lactyl-),
cyclo(-N-methyl-D-alanyl-D-lactyl-N-methyl-D-isoleucyl-
L-lactyl-N-methyl-D-2-aminobutyryl -L-lactyl-),
cyclo(-N-methyl-D-alanyl-D-lactyl-N-methyl-D-isoleucyl-
D-lactyl-N-methyl-L-2-aminobutyryl -L-lactyl-),
cyclo(-N-methyl-D-alanyl-D-lactyl-N-methyl-L-isoleucyl-
L-lactyl-N-methyl-L-2-aminobutyryl-L-lactyl-),
cyclo(-N-methyl-D-alanyl-L-lactyl-N-methyl-D-isoleucyl-
L-lactyl-N-methyl-L-2-aminobutyryl-L-lactyl-),
cyclo(-N-methyl-D-alanyl-L-lactyl-N-methyl-L-isoleucyl-
D-lactyl-N-methyl-L-2-aminobutyryl-L-lactyl-),
cyclo(-N-methyl-D-alanyl-L-lactyl-N-methyl-L-isoleucyl-
L-lactyl-N-methyl-L-2-aminobutyryl-D-lactyl-),
cyclo(-N-methyl-L-alanyl-D-lactyl-N-methyl-D-isoleucyl-
L-lactyl-N-methyl-L-2-aminobutyryl-L-lactyl-),
cyclo(-N-methyl-L-alanyl-D-lactyl-N-methyl-L-isoleucyl-
D-lactyl-N-methyl-L-2-aminobutyryl-L-lactyl-),
cyclo(-N-methyl-L-alanyl-D-lactyl-N-methyl-L-isoleucyl-
L-lactyl-N-methyl-D-2-aminobutyryl-L-lactyl-),
cyclo(-N-methyl-L-alanyl-L-lactyl-N-methyl-D-isoleucyl-
D-lactyl-N-methyl-L-2-aminobutyryl-L-lactyl-),
cyclo(-N-methyl-L-alanyl-L-lactyl-N-methyl-L-isoleucyl-
L-lactyl-N-methyl-D-2-aminobutyryl-L-lactyl-),
cyclo(-N-methyl-L-alanyl-L-lactyl-N-methyl-L-isoleucyl-
L-lactyl-N-methyl-L-2-aminobutyryl-D-lactyl-),
cyclo(-N-methyl-D-alanyl-D-lactyl-N-methyl-L-isoleucyl-
L-lactyl-N-methyl-L-2-aminobutyryl-D-lactyl-),
cyclo(-N-methyl-L-alanyl-L-lactyl-N-methyl-L-isoleucyl-
L-lactyl-N-methyl-D-2-aminobutyryl-D-lactyl-),
cyclo(-N-methyl-L-alanyl-D-lactyl-N-methyl-L-isoleucyl-
L-lactyl-N-methyl-L-2-aminobutyryl-D-lactyl-),
cyclo(-N-methyl-L-alanyl-D-lactyl-N-methyl-L-isoleucyl-
L-lactyl-N-methyl-D-2-aminobutyryl-D-lactyl-),
cyclo(-N-methyl-L-alanyl-D-lactyl-N-methyl-L-isoleucyl-
D-lactyl-N-methyl-D-2-aminobutyryl-L-lactyl-),
cyclo(-N-methyl-L-alanyl-D-lactyl-N-methyl-L-isoleucyl-
D-lactyl-N-methyl-D-2-aminobutyryl-D-lactyl-),
cyclo(-N-methyl-D-alanyl-L-lactyl-N-methyl-L-isoleucyl-
L-lactyl-N-methyl-D-2-aminobutyryl-D-lactyl-),
cyclo(-N-methyl-D-alanyl-D-lactyl-N-methyl-L-isoleucyl-
L-lactyl-N-methyl-D-2-aminobutyryl-L-lactyl-),
cyclo(-N-methyl-D-alanyl-L-lactyl-N-methyl-L-isoleucyl-
L-lactyl-N-methyl-D-2-aminobutyryl-L-lactyl-),
cyclo(-N-methyl-D-alanyl-L-lactyl-N-methyl-D-isoleucyl-
D-lactyl-N-methyl-L-2-aminobutyryl-L-lactyl-),
cyclo(-N-methyl-D-alanyl-L-lactyl-N-methyl-D-isoleucyl-
L-lactyl-N-methyl-L-2-aminobutyryl-L-lactyl-),
cyclo(-N-methyl-D-alanyl-D-lactyl-N-methyl-L-isoleucyl-
L-lactyl-N-methyl-L-2-aminobutyryl-L-lactyl-),
cyclo(-N-methyl-D-alanyl-D-lactyl-N-methyl-L-isoleucyl-
D-lactyl-N-methyl-L-2-aminobutyryl-L-lactyl-),
cyclo(-N-methyl-L-alanyl-L-lactyl-N-methyl-D-isoleucyl-
D-lactyl-N-methyl-D-2-aminobutyryl-L-lactyl-), cyclo(-N-methyl-L-alanyl-D-lactyl-N-methyl-D-isoleucyl-
L-lactyl-N-methyl-D-2-aminobutyryl-L-lactyl-),
cyclo(-N-methyl-L-alanyl-L-lactyl-N-methyl-D-isoleucyl-
D-lactyl-N-methyl-L-2-aminobutyryl-D-lactyl-),
cyclo(-N-methyl-L-alanyl-L-lactyl-N-methyl-D-isoleucyl-
L-lactyl-N-methyl-D-2-aminobutyryl-D-lactyl-),
cyclo(-N-methyl-L-alanyl-D-lactyl-N-methyl-D-isoleucyl-
D-lactyl-N-methyl-L-norvalyl-D-lactyl-),
cyclo(-N-methyl-L-alanyl-D-lactyl-N-methyl-L-isoleucyl-
D-lactyl-N-methyl-L-norvalyl-D-lactyl-),
cyclo(-N-methyl-L-alanyl-D-lactyl-N-methyl-L-
alloisoleucyl-D-lactyl-N-methyl-L-norvalyl-D-lactyl-),
cyclo(-N-methyl-L-alanyl-D-lactyl-N-methyl-L-isoleucyl-
L-lactyl-N-methyl-L-norvalyl-D-lactyl-),
cyclo(-N-methyl-L-alanyl-L-lactyl-N-methyl-D-isoleucyl-
L-lactyl-N-methyl-L-norvalyl-D-lactyl-),
cyclo(-N-methyl-D-alanyl-L-lactyl-N-methyl-D-isoleucyl-
D-lactyl-N-methyl-D-norvalyl-L-lactyl-),
cyclo(-N-methyl-D-alanyl-L-lactyl-N-methyl-D-isoleucyl-
L-lactyl-N-methyl-D-norvalyl-L-lactyl-),
cyclo(-N-methyl-D-alanyl-L-lactyl-N-methyl-L-isoleucyl-
D-lactyl-N-methyl-D-norvalyl-L-lactyl-),
cyclo(-N-methyl-D-alanyl-L-lactyl-N-methyl-D-isoleucyl-
L-lactyl-N-methyl-D-norvalyl-L-lactyl-),
cyclo(-N-methyl-D-alanyl-L-lactyl-N-methyl-D-
alloisoleucyl-L-lactyl-N-methyl-D-norvalyl-L-lactyl-),
cyclo(-N-methyl-L-alanyl-D-lactyl-N-methyl-D-isoleucyl-
D-lactyl-N-methyl-L-valyl-D-lactyl-),
cyclo(-N-methyl-L-alanyl-D-lactyl-N-methyl-L-isoleucyl-
D-lactyl-N-methyl-L-valyl-D-lactyl-),
cyclo(-N-methyl-L-alanyl-D-lactyl-N-methyl-L-
alloisoleucyl-D-lactyl-N-methyl-L-valyl-D-lactyl-),
cyclo(-N-methyl-L-alanyl-D-lactyl-N-methyl-L-isoleucyl-
L-lactyl-N-methyl-L-valyl-D-lactyl-),
cyclo(-N-methyl-L-alanyl-L-lactyl-N-methyl-D-isoleucyl-
L-lactyl-N-methyl-L-valyl-D-lactyl-),
cyclo(-N-methyl-D-alanyl-L-lactyl-N-methyl-D-isoleucyl-
D-lactyl-N-methyl-D-valyl-L-lactyl-),
cyclo(-N-methyl-D-alanyl-L-lactyl-N-methyl-L-isoleucyl-
L-lactyl-N-methyl-D-valyl-L-lactyl-),
cyclo(-N-methyl-D-alanyl-L-lactyl-N-methyl-L-isoleucyl-
D-lactyl-N-methyl-D-valyl-L-lactyl-),
cyclo(-N-methyl-D-alanyl-L-lactyl-N-methyl-D-isoleucyl-
L-lactyl-N-methyl-D-valyl-L-lactyl-),
cyclo(-N-methyl-D-alanyl-L-lactyl-N-methyl-D-
alloisoleucyl-L-lactyl-N-methyl-D-valyl-L-lactyl-),
cyclo(-N-methyl-L-alanyl-D-lactyl-N-methyl-D-isoleucyl-
D-lactyl-N-methyl-L-norleucyl-D-lactyl-),
cyclo(-N-methyl-L-alanyl-D-lactyl-N-methyl-L-isoleucyl-
D-lactyl-N-methyl-L-norleucyl-D-lactyl-),
cyclo(-N-methyl-L-alanyl-D-lactyl-N-methyl-L-
alloisoleucyl-D-lactyl-N-methyl-L-norleucyl-D-lactyl-),
cyclo(-N-methyl-L-alanyl-D-lactyl-N-methyl-L-isoleucyl-
L-lactyl-N-methyl-L-norleucyl-D-lactyl-),
cyclo(-N-methyl-L-alanyl-L-lactyl-N-methyl-D-isoleucyl-
L-lactyl-N-methyl-L-norleucyl-D-lactyl-),
cyclo(-N-methyl-D-alanyl-L-lactyl-N-methyl-D-isoleucyl-
D-lactyl-N-methyl-D-norleucyl-L-lactyl-),
cyclo(-N-methyl-D-alanyl-L-lactyl-N-methyl-L-isoleucyl-
L-lactyl-N-methyl-D-norleucyl-L-lactyl-),
cyclo(-N-methyl-D-alanyl-L-lactyl-N-methyl-L-isoleucyl-
D-lactyl-N-methyl-D-norleucyl-L-lactyl-),
cyclo(-N-methyl-D-alanyl-L-lactyl-N-methyl-D-isoleucyl-
L-lactyl-N-methyl-D-norleucyl-L-lactyl-),
cyclo(-N-methyl-D-alanyl-L-lactyl-N-methyl-D-
alloisoleucyl-L-lactyl-N-methyl-D-norleucyl-L-lactyl-),
cyclo(-N-methyl-L-alanyl-D-lactyl-N-methyl-D-isoleucyl-
D-lactyl-N-methyl-L-leucyl-D-lactyl-),
cyclo(-N-methyl-L-alanyl-D-lactyl-N-methyl-L-isoleucyl-
D-lactyl-N-methyl-L-leucyl-D-lactyl-),
cyclo(-N-methyl-L-alanyl-D-lactyl-N-methyl-L-
alloisoleucyl-D-lactyl-N-methyl-L-leucyl-D-lactyl-),
cyclo(-N-methyl-L-alanyl-D-lactyl-N-methyl-L-isoleucyl-
L-lactyl-N-methyl-L-leucyl-D-lactyl-),
cyclo(-N-methyl-L-alanyl-L-lactyl-N-methyl-D-isoleucyl-
L-lactyl-N-methyl-L-leucyl-D-lactyl-),
cyclo(-N-methyl-D-alanyl-L-lactyl-N-methyl-D-isoleucyl-
D-lactyl-N-methyl-D-leucyl-L-lactyl-),
cyclo(-N-methyl-D-alanyl-L-lactyl-N-methyl-L-isoleucyl-
L-lactyl-N-methyl-D-leucyl-L-lactyl-),
cyclo(-N-methyl-D-alanyl-L-lactyl-N-methyl-L-isoleucyl-
D-lactyl-N-methyl-D-leucyl-L-lactyl-),
cyclo(-N-methyl-D-alanyl-L-lactyl-N-methyl-D-isoleucyl-
L-lactyl-N-methyl-D-leucyl-L-lactyl-),
cyclo(-N-methyl-D-alanyl-L-lactyl-N-methyl-D-
alloisoleucyl-L-lactyl-N-methyl-D-leucyl-L-lactyl-),
cyclo(-N-methyl-L-alanyl-D-lactyl-N-methyl-D-isoleucyl-
D-lactyl-N-methyl-D-isoleucyl-D-lactyl-),
cyclo(-N-methyl-D-alanyl-L-lactyl-N-methyl-D-isoleucyl-
D-lactyl-N-methyl-D-isoleucyl-D-lactyl-),
cyclo(-N-methyl-D-alanyl-D-lactyl-N-methyl-L-isoleucyl-
D-lactyl-N-methyl-D-isoleucyl-D-lactyl-),
cyclo(-N-methyl-D-alanyl-D-lactyl-N-methyl-D-isoleucyl-
L-lactyl-N-methyl-D-isoleucyl-D-lactyl-),
cyclo(-N-methyl-D-alanyl-D-lactyl-N-methyl-D-isoleucyl-
D-lactyl-N-methyl-L-isoleucyl-D-lactyl-),
cyclo(-N-methyl-D-alanyl-D-lactyl-N-methyl-D-isoleucyl-
D-lactyl-N-methyl-D-isoleucyl-L-lactyl-),
cyclo(-N-methyl-D-alanyl-D-lactyl-N-methyl-D-isoleucyl-
D-lactyl-N-methyl-D-isoleucyl-D-lactyl-),
cyclo(-N-methyl-L-alanyl-L-lactyl-N-methyl-L-isoleucyl-
L-lactyl-N-methyl-L-isoleucyl-L-lactyl-),
cyclo(-N-methyl-L-alanyl-D-lactyl-N-methyl-L-isoleucyl-
L-lactyl-N-methyl-L-isoleucyl-L-lactyl-),
cyclo(-N-methyl-L-alanyl-L-lactyl-N-methyl-D-isoleucyl-
L-lactyl-N-methyl-L-isoleucyl-L-lactyl-),
cyclo(-N-methyl-L-alanyl-L-lactyl-N-methyl-L-isoleucyl-
D-lactyl-N-methyl-L-isoleucyl-L-lactyl-),
cyclo(-N-methyl-L-alanyl-L-lactyl-N-methyl-L-isoleucyl-
L-lactyl-N-methyl-D-isoleucyl-L-lactyl-),
cyclo(-N-methyl-L-alanyl-L-lactyl-N-methyl-L-isoleucyl-
L-lactyl-N-methyl-L-isoleucyl-D-lactyl-),
cyclo(-N-methyl-L-alanyl-L-lactyl-N-methyl-L-isoleucyl-
L-lactyl-N-methyl-L-isoleucyl-L-lactyl-),
cyclo(-N-methyl-L-alanyl-L-lactyl-N-methyl-D-isoleucyl-
D-lactyl-N-methyl-D-isoleucyl-D-lactyl-),
cyclo(-N-methyl-L-alanyl-D-lactyl-N-methyl-L-isoleucyl-
D-lactyl-N-methyl-D-isoleucyl-D-lactyl-),
cyclo(-N-methyl-L-alanyl-D-lactyl-N-methyl-D-isoleucyl-
L-lactyl-N-methyl-D-isoleucyl-D-lactyl-),
cyclo(-N-methyl-L-alanyl-D-lactyl-N-methyl-D-isoleucyl-
D-lactyl-N-methyl-D-isoleucyl-L-lactyl-),
cyclo(-N-methyl-D-alanyl-L-lactyl-N-methyl-L-isoleucyl-
D-lactyl-N-methyl-D-isoleucyl-D-lactyl-),
cyclo(-N-methyl-D-alanyl-L-lactyl-N-methyl-D-isoleucyl-
L-lactyl-N-methyl-D-isoleucyl-D-lactyl-),
cyclo(-N-methyl-D-alanyl-L-lactyl-N-methyl-D-isoleucyl-
D-lactyl-N-methyl-L-alanyl-D-lactyl-),
cyclo(-N-methyl-D-alanyl-D-lactyl-N-methyl-L-isoleucyl-
L-lactyl-N-methyl-D-isoleucyl-D-lactyl-),
cyclo(-N-methyl-D-alanyl-D-lactyl-N-methyl-L-isoleucyl-
D-lactyl-N-methyl-L-isoleucyl-D-lactyl-),
cyclo(-N-methyl-D-alanyl-D-lactyl-N-methyl-D-isoleucyl-
L-lactyl-N-methyl-D-isoleucyl-L-lactyl-),
cyclo(-N-methyl-D-alanyl-D-lactyl-N-methyl-D-isoleucyl-
L-lactyl-N-methyl-L-isoleucyl-D-lactyl-), cyclo(-N-methyl-D-alanyl-D-lactyl-N-methyl-D-isoleucyl-L-lactyl-N-methyl-D-isoleucyl-L-lactyl-),
cyclo(-N-methyl-D-alanyl-D-lactyl-N-methyl-D-isoleucyl-D-lactyl-N-methyl-L-isoleucyl-L-lactyl-),
cyclo(-N-methyl-D-alanyl-D-lactyl-N-methyl-L-isoleucyl-L-lactyl-N-methyl-L-isoleucyl-L-lactyl-),
cyclo(-N-methyl-D-alanyl-L-lactyl-N-methyl-D-isoleucyl-L-lactyl-N-methyl-L-isoleucyl-L-lactyl-),
cyclo(-N-methyl-D-alanyl-L-lactyl-N-methyl-L-isoleucyl-D-lactyl-N-methyl-L-isoleucyl-L-lactyl-),
cyclo(-N-methyl-D-alanyl-L-lactyl-N-methyl-L-isoleucyl-L-lactyl-N-methyl-L-isoleucyl-D-lactyl-),
cyclo(-N-methyl-L-alanyl-D-lactyl-N-methyl-D-isoleucyl-L-lactyl-N-methyl-L-isoleucyl-L-lactyl-),
cyclo(-N-methyl-L-alanyl-D-lactyl-N-methyl-L-isoleucyl-D-lactyl-N-methyl-L-isoleucyl-L-lactyl-),
cyclo(-N-methyl-L-alanyl-D-lactyl-N-methyl-L-isoleucyl-L-lactyl-N-methyl-D-isoleucyl-L-lactyl-),
cyclo(-N-methyl-L-alanyl-L-lactyl-N-methyl-D-isoleucyl-D-lactyl-N-methyl-L-isoleucyl-L-lactyl-),
cyclo(-N-methyl-L-alanyl-L-lactyl-N-methyl-D-isoleucyl-L-lactyl-N-methyl-D-isoleucyl-L-lactyl-),
cyclo(-N-methyl-L-alanyl-L-lactyl-N-methyl-D-isoleucyl-L-lactyl-N-methyl-L-isoleucyl-D-lactyl-),
cyclo(-N-methyl-L-alanyl-L-lactyl-N-methyl-L-isoleucyl-D-lactyl-N-methyl-D-isoleucyl-L-lactyl-),
cyclo(-N-methyl-L-alanyl-L-lactyl-N-methyl-L-isoleucyl-D-lactyl-N-methyl-L-isoleucyl-D-lactyl-),
cyclo(-N-methyl-L-alanyl-L-lactyl-N-methyl-L-isoleucyl-L-lactyl-N-methyl-D-isoleucyl-D-lactyl-),
cyclo(-N-methyl-L-alanyl-L-lactyl-N-methyl-L-isoleucyl-D-lactyl-N-methyl-D-isoleucyl-D-lactyl-),
cyclo(-N-methyl-D-alanyl-L-lactyl-N-methyl-L-isoleucyl-L-lactyl-N-methyl-D-isoleucyl-D-lactyl-),
cyclo(-N-methyl-D-alanyl-D-lactyl-N-methyl-L-isoleucyl-L-lactyl-N-methyl-L-isoleucyl-D-lactyl-),
cyclo(-N-methyl-D-alanyl-D-lactyl-N-methyl-D-isoleucyl-L-lactyl-N-methyl-L-isoleucyl-L-lactyl-),
cyclo(-N-methyl-L-alanyl-D-lactyl-N-methyl-L-isoleucyl-L-lactyl-N-methyl-D-isoleucyl-D-lactyl-),
cyclo(-N-methyl-L-alanyl-D-lactyl-N-methyl-D-isoleucyl-L-lactyl-N-methyl-L-isoleucyl-L-lactyl-),
cyclo(-N-methyl-L-alanyl-D-lactyl-N-methyl-D-isoleucyl-D-lactyl-N-methyl-L-isoleucyl-L-lactyl-),
cyclo(-N-methyl-L-alanyl-D-lactyl-N-methyl-D-isoleucyl-D-lactyl-N-methyl-D-isoleucyl-L-lactyl-),
cyclo(-N-methyl-D-alanyl-L-lactyl-N-methyl-L-isoleucyl-D-lactyl-N-methyl-L-isoleucyl-D-lactyl-),
cyclo(-N-methyl-D-alanyl-L-lactyl-N-methyl-D-isoleucyl-L-lactyl-N-methyl-L-isoleucyl-D-lactyl-),
cyclo(-N-methyl-D-alanyl-L-lactyl-N-methyl-D-isoleucyl-D-lactyl-N-methyl-L-isoleucyl-L-lactyl-),
cyclo(-N-methyl-D-alanyl-D-lactyl-N-methyl-L-isoleucyl-L-lactyl-N-methyl-D-isoleucyl-L-lactyl-),
cyclo(-N-methyl-D-alanyl-D-lactyl-N-methyl-L-isoleucyl-D-lactyl-N-methyl-L-isoleucyl-L-lactyl-),
cyclo(-N-methyl-L-alanyl-L-lactyl-N-methyl-D-isoleucyl-D-lactyl-N-methyl-D-isoleucyl-L-lactyl-),
cyclo(-N-methyl-L-alanyl-D-lactyl-N-methyl-D-isoleucyl-L-lactyl-N-methyl-D-isoleucyl-L-lactyl-),
cyclo(-N-methyl-L-alanyl-L-lactyl-N-methyl-D-isoleucyl-D-lactyl-N-methyl-L-isoleucyl-D-lactyl-),
cyclo(-N-methyl-L-alanyl-L-lactyl-N-methyl-D-isoleucyl-L-lactyl-N-methyl-D-isoleucyl-D-lactyl-),
cyclo(-N-methyl-L-alanyl-D-lactyl-N-methyl-D-isoleucyl-D-lactyl-N-methyl-D-isoleucyl-D-lactyl-).

If, for example, N-methyl-L-alanyl-D-lactyl-N-methyl-L-isoleucyl-D-lactyl-N-methyl-L-isoleucyl-D-lactic acid is employed as compounds of the formula (II) in accordance with process 2 for the preparation of the new cyclic hexadepsipeptides of the formula (I), the process can be represented by the following equation:

Formula (II) provides a general definition of the open-chain hexadepsipeptides required as starting substances for carrying out the process. In this formula, $R^1$ to $R^3$ preferably represent those radicals which have already been mentioned in connection with the description of the substances of the formula (I) according to the invention as being preferred for these substituents.

The open-chain hexadepsipeptides of the formula (II) used as starting materials are described in an earlier, but not prior-published, patent application (cf. German Patent Application P 4 317 458.2).

The following stereoisomeric compounds of the general formula (II) may be mentioned individually:

N-methyl-L-alanyl-D-lactyl-N-methyl-L-isoleucyl-D-lactyl-N-methyl-glycyl-D-lactic acid,
N-methyl-L-alanyl-D-lactyl-N-methyl-L-alloisoleucyl-D-lactyl-N-methyl-glycyl-D-lactic acid,
N-methyl-L-isoleucyl-D-lactyl-N-methyl-glycyl-D-lactyl-N-methyl-L-alanyl-D-lactic acid,
N-methyl-L-alloisoleucyl-D-lactyl-N-methyl-glycyl-D-lactyl-N-methyl-L-alanyl-D-lactic acid,
N-methyl-glycyl-D-lactyl-N-methyl-L-alanyl-D-lactyl-N-methyl-L-alloisoleucyl-D-lactic acid,
N-methyl-glycyl-D-lactyl-N-methyl-D-alanyl-D-lactyl-N-methyl-L-alloisoleucyl-D-lactic acid,
N-methyl-glycyl-L-lactyl-N-methyl-D-alanyl-L-lactyl-N-methyl-D-alloisoleucyl-L-lactic acid,
N-methyl-L-alanyl-D-lactyl-N-methyl-D-isoleucyl-D-lactyl-N-methyl-L-alanyl-D-lactic acid,
N-methyl-L-alanyl-D-lactyl-N-methyl-L-alloisoleucyl-D-lactyl-N-methyl-L-alanyl-D-lactic acid,
N-methyl-L-alanyl-D-lactyl-N-methyl-L-isoleucyl-L-lactyl-N-methyl-L-alanyl-D-lactic acid,
N-methyl-L-alanyl-D-lactyl-N-methyl-D-isoleucyl-L-lactyl-N-methyl-L-alanyl-D-lactic acid, N-methyl-D-alanyl-L-lactyl-N-methyl-D-isoleucyl-D-
lactyl-N-methyl-D-alanyl-L-lactic acid,
N-methyl-D-alanyl-L-lactyl-N-methyl-L-isoleucyl-L-
lactyl-N-methyl-D-alanyl-L-lactic acid,
N-methyl-D-alanyl-L-lactyl-N-methyl-L-isoleucyl-D-
lactyl-N-methyl-D-alanyl-L-lactic acid,
N-methyl-D-alanyl-L-lactyl-N-methyl-D-isoleucyl-L-
lactyl-N-methyl-D-alanyl-L-lactic acid,
N-methyl-D-alanyl-L-lactyl-N-methyl-D-alloisoleucyl-L-
lactyl-N-methyl-D-alanyl-L-lactic acid,
N-methyl-L-2-aminobutyryl-D-lactyl-N-methyl-D-alanyl-
D-lactyl-N-methyl-L-isoleucyl-D-lactic acid,
N-methyl-L-alanyl-D-lactyl-N-methyl-L-isoleucyl-D-
lactyl-N-methyl-L-2-aminobutyryl-D-lactic acid,
N-methyl-L-isoleucyl-D-lactyl-N-methyl-L-2-
aminobutyryl-D-lactyl-N-methyl-L-alanyl-D-lactic acid,
N-methyl-L-2-aminobutyryl-D-lactyl-N-methyl-L-alanyl-
D-lactyl-N-methyl-L-alloisoleucyl-D-lactic acid,
N-methyl-L-2-aminobutyryl-D-lactyl-N-methyl-L-alanyl-
D-lactyl-N-methyl-D-isoleucyl-L-lactic acid,
N-methyl-L-2-aminobutyryl-D-lactyl-N-methyl-L-alanyl-
D-lactyl-N-methyl-L-isoleucyl-D-lactic acid,
N-methyl-D-2-aminobutyryl-L-lactyl-N-methyl-D-alanyl-
D-lactyl-N-methyl-D-isoleucyl-L-lactic acid,
N-methyl-D-2-aminobutyryl-L-lactyl-N-methyl-D-alanyl-
L-lactyl-N-methyl-L-isoleucyl-L-lactic acid,
N-methyl-D-2-aminobutyryl-L-lactyl-N-methyl-D-alanyl-
L-lactyl-N-methyl-L-isoleucyl-D-lactic acid,
N-methyl-D-2-aminobutyryl-L-lactyl-N-methyl-D-alanyl-
L-lactyl-N-methyl-D-isoleucyl-L-lactic acid,
N-methyl-D-2-aminobutyryl-L-lactyl-N-methyl-D-alanyl-
L-lactyl-N-methyl-D-alloisoleucyl-L-lactic acid,
N-methyl-L-norvalyl-D-lactyl-N-methyl-D-alanyl-D-lactyl-
N-methyl-L-isoleucyl-D-lactic acid,
N-methyl-L-alanyl-D-lactyl-N-methyl-L-isoleucyl-D-
lactyl-N-methyl-L-norvalyl-D-lactic acid,
N-methyl-L-isoleucyl-D-lactyl-N-methyl-L-norvalyl-D-
lactyl-N-methyl-L-alanyl-D-lactic acid,
N-methyl-L-norvalyl-D-lactyl-N-methyl-L-alanyl-D-lactyl-
N-methyl-L-alloisoleucyl-D-lactic acid,
N-methyl-L-norvalyl-D-lactyl-N-methyl-L-alanyl-D-lactyl-
N-methyl-D-isoleucyl-L-lactic acid,
N-methyl-L-norvalyl-D-lactyl-N-methyl-L-alanyl-D-lactyl-
N-methyl-L-isoleucyl-D-lactic acid,
N-methyl-D-norvalyl-L-lactyl-N-methyl-D-alanyl-L-lactyl-
N-methyl-D-isoleucyl-L-lactic acid,
N-methyl-D-norvalyl-L-lactyl-N-methyl-D-alanyl-L-lactyl-
N-methyl-L-isoleucyl-L-lactic acid,
N-methyl-D-norvalyl-L-lactyl-N-methyl-D-alanyl-L-lactyl-
N-methyl-L-isoleucyl-D-lactic acid,
N-methyl-D-norvalyl-L-lactyl-N-methyl-D-alanyl-L-lactyl-
N-methyl-D-isoleucyl-L-lactic acid,
N-methyl-D-norvalyl-L-lactyl-N-methyl-D-alanyl-L-lactyl-
N-methyl-D-alloisoleucyl-L-lactic acid,
N-methyl-L-valyl-D-lactyl-N-methyl-D-alanyl-D-lactyl-N-
methyl-L-isoleucyl-D-lactic acid,
N-methyl-L-alanyl-D-lactyl-N-methyl-L-isoleucyl-D-
lactyl-N-methyl-L-valyl-D-lactic acid,
N-methyl-L-isoleucyl-D-lactyl-N-methyl-L-valyl-D-lactyl-
N-methyl-L-alanyl-D-lactic acid,
N-methyl-L-valyl-D-lactyl-N-methyl-L-alanyl-D-lactyl-N-
methyl-L-alloisoleucyl-D-lactic acid,
N-methyl-L-valyl-D-lactyl-N-methyl-L-alanyl-D-lactyl-N-
methyl-D-isoleucyl-L-lactic acid,
N-methyl-L-valyl-D-lactyl-N-methyl-L-alanyl-D-lactyl-N-
methyl-L-isoleucyl-D-lactic acid,
N-methyl-D-valyl-L-lactyl-N-methyl-D-alanyl-L-lactyl-N-
methyl-D-isoleucyl-L-lactic acid,
N-methyl-D-valyl-L-lactyl-N-methyl-D-alanyl-L-lactyl-N-
methyl-L-isoleucyl-L-lactic acid,
N-methyl-D-valyl-L-lactyl-N-methyl-D-alanyl-L-lactyl-N-
methyl-L-isoleucyl-D-lactic acid,
N-methyl-D-valyl-L-lactyl-N-methyl-D-alanyl-L-lactyl-N-
methyl-D-isoleucyl-L-lactic acid,
N-methyl-D-valyl-L-lactyl-N-methyl-D-alanyl-L-lactyl-N-
methyl-D-alloisoleucyl-L-lactic acid,
N-methyl-L-norleucyl-D-lactyl-N-methyl-D-alanyl-D-
lactyl-N-methyl-L-isoleucyl-D-lactic acid,
N-methyl-L-alanyl-D-lactyl-N-methyl-L-isoleucyl-D-
lactyl-N-methyl-L-norleucyl-D-lactic acid,
N-methyl-L-isoleucyl-D-lactyl-N-methyl-L-norleucyl-D-
lactyl-N-methyl-L-alanyl-D-lactic acid,
N-methyl-L-norleucyl-D-lactyl-N-methyl-L-alanyl-D-
lactyl-N-methyl-L-alloisoleucyl-D-lactic acid,
N-methyl-L-norleucyl-D-lactyl-N-methyl-L-alanyl-D-
lactyl-N-methyl-D-isoleucyl-L-lactic acid,
N-methyl-L-norleucyl-D-lactyl-N-methyl-L-alanyl-D-
lactyl-N-methyl-L-isoleucyl-D-lactic acid,
N-methyl-D-norleucyl-L-lactyl-N-methyl-D-alanyl-D-
lactyl-N-methyl-D-isoleucyl-L-lactic acid,
N-methyl-D-norleucyl-L-lactyl-N-methyl-D-alanyl-L-
lactyl-N-methyl-L-isoleucyl-L-lactic acid,
N-methyl-D-norleucyl-L-lactyl-N-methyl-D-alanyl-L-
lactyl-N-methyl-L-isoleucyl-D-lactic acid,
N-methyl-D-norleucyl-L-lactyl-N-methyl-D-alanyl-L-
lactyl-N-methyl-D-isoleucyl-L-lactic acid,
N-methyl-D-norleucyl-L-lactyl-N-methyl-D-alanyl-L-
lactyl-N-methyl-D-alloisoleucyl-L-lactic acid,
N-methyl-L-leucyl-D-lactyl-N-methyl-D-alanyl-D-lactyl-
N-methyl-L-isoleucyl-D-lactic acid,
N-methyl-L-alanyl-D-lactyl-N-methyl-L-isoleucyl-D-
lactyl-N-methyl-L-leucyl-D-lactic acid,
N-methyl-L-leucyl-D-lactyl-N-methyl-L-norleucyl-D-
lactyl-N-methyl-L-alanyl-D-lactic acid,
N-methyl-L-leucyl-D-lactyl-N-methyl-L-alanyl-D-lactyl-
N-methyl-L-alloisoleucyl-D-lactic acid,
N-methyl-L-leucyl-D-lactyl-N-methyl-L-alanyl-D-lactyl-
N-methyl-D-isoleucyl-L-lactic acid,
N-methyl-L-leucyl-D-lactyl-N-methyl-L-alanyl-D-lactyl-
N-methyl-L-isoleucyl-D-lactic acid,
N-methyl-D-leucyl-L-lactyl-N-methyl-D-alanyl-D-lactyl-
N-methyl-D-isoleucyl-L-lactic acid,
N-methyl-D-leucyl-L-lactyl-N-methyl-D-alanyl-L-lactyl-
N-methyl-L-isoleucyl-L-lactic acid,
N-methyl-D-leucyl-L-lactyl-N-methyl-D-alanyl-L-lactyl-
N-methyl-L-isoleucyl-D-lactic acid,
N-methyl-D-leucyl-L-lactyl-N-methyl-D-alanyl-L-lactyl-
N-methyl-D-isoleucyl-L-lactic acid,
N-methyl-D-leucyl-L-lactyl-N-methyl-D-alanyl-L-lactyl-
N-methyl-D-alloisoleucyl-L-lactic acid,
N-methyl-L-alanyl-D-lactyl-N-methyl-D-isoleucyl-D-
lactyl-N-methyl-D-isoleucyl-D-lactic acid,
N-methyl-L-alloisoleucyl-D-lactyl-N-methyl-L-alanyl-D-
lactyl-N-methyl-L-isoleucyl-D-lactic acid,
N-methyl-L-alanyl-D-lactyl-N-methyl-L-isoleucyl-D-
lactyl-N-methyl-L-alloisoleucyl-D-lactic acid,
N-methyl-L-alanyl-D-lactyl-N-methyl-L-alloisoleucyl-D-
lactyl-N-methyl-L-alloisoleucyl-D-lactic acid,
N-methyl-L-alanyl-D-lactyl-N-methyl-L-isoleucyl-L-
lactyl-N-methyl-L-isoleucyl-D-lactic acid,
N-methyl-L-alanyl-D-lactyl-N-methyl-D-isoleucyl-L-
lactyl-N-methyl-L-isoleucyl-D-lactic acid,
N-methyl-D-alanyl-L-lactyl-N-methyl-D-isoleucyl-D-
lactyl-N-methyl-D-isoleucyl-D-lactic acid,
N-methyl-D-alanyl-L-lactyl-N-methyl-L-isoleucyl-L-
lactyl-N-methyl-D-isoleucyl-L-lactic acid, N-methyl-D-alanyl-L-lactyl-N-methyl-L-isoleucyl-D-lactyl-N-methyl-D-isoleucyl-L-lactic acid, N-methyl-D-alanyl-L-lactyl-N-methyl-D-isoleucyl-L-lactyl-N-methyl-D-isoleucyl-L-lactic acid, N-methyl-D-alanyl-L-lactyl-N-methyl-D-alloisoleucyl-L-lactyl-N-methyl-D-isoleucyl-L-lactic acid, N-methyl-D-alanyl-L-lactyl-N-methyl-D-isoleucyl-L-lactyl-N-methyl-D-alloisoleucyl-L-lactic acid, N-methyl-D-alanyl-L-lactyl-N-methyl-D-alloisoleucyl-L-lactyl-N-methyl-D-alloisoleucyl-L-lactic acid.

The cyclization of the compounds of the formula (II) is preferably carried out in the presence of suitable coupling reagents and in the presence of a basic reaction auxiliary in a diluent under high-dilution conditions.

Coupling reagents used for carrying out process 2 are all those which are suitable for producing amide linkage (cf., for example: Houben-Weyl, Methoden der organischen Chemie [Methods in Organic Chemistry], Volume 15/2; Bodanszky et al., Peptide Synthesis 2nd ed. (Wiley & Sons, New York 1976) or Gross, Meienhofer, The Peptides: Analysis synthesis, biology (Academic Press, New York 1979). The following methods are preferably used: the active ester method using pentachlorophenol (Pcp) and pentafluorophenol (Pfp), N-hydroxysuccinimide, N-hydroxy-5-norbornene-2,3-dicarboxamide (HONB), 1-hydroxybenzotriazole (HOBt) or 3-hydroxy-4-oxo-3,4-dihydro-1,2,3-benzotriazine as the alcohol component, coupling with carbodiimides, such as dicyclohexylcarbodiimide (DCC) using the DCC additive process, or using n-propanephosphonic anhydride (PPA), and the mixed anhydride process using pivaloyl chloride, ethyl chloroformate (EEDQ) and isobutyl chloroformate (IIDQ), or coupling with phosphonium reagents, such as benzotriazol-1-yl-oxy-tris(dimethylamino-phosphonium) hexafluorophosphate (BOP), bis(2-oxo-3-oxazolidinyl) phosphinic chloride (BOP-Cl), or with phosphonic ester reagents, such as diethyl cyanophosphonate (DEPC) and diphenylphosphoryl azide (DPPA) or uronium reagents, such as 2-(1H-benzotriazol-1-yl)-1,1,3,3-tetramethyluronium tetrafluoroborate (TBTU).

The coupling reaction with phosphonium reagents, such as bis(2-oxo-3-oxazolidinyl) phosphinic chloride (BOP-Cl), benzotriazol-1-yl-oxy-tris(dimethylamino-phosphonium) hexafluorophosphate (BOP), and phosphonic ester reagents, such as diethyl cyanophosphonate (DEPC) or diphenylphosphoryl azide (DPPA), is preferred.

Basic reaction auxiliaries which can be employed are all suitable acid-binding agents, such as amines, in particular tertiary amines, and alkali metal and alkaline earth metal compounds.

Examples which may be mentioned are the hydroxides, oxides and carbonates of lithium, sodium, potassium, magnesium, calcium and barium, furthermore other basic compounds, such as triethylamine, trimethylamine, tribenzylamine, triisopropylamine, tributylamine, tribenzylamine, tricyclohexylamine, triamylamine, trihexylamine, N,N-dimethyl-aniline, N,N-di-methyl-toluidine, N,N-dimethyl-p-aminopyridine, N-methyl-1-pyrrolidine, N-methylpiperidine, N-methyl-imidazole, N-methyl-pyrrole, N-methyl-morpholine, N-methyl-hexamethyleneimine, pyridine, 4-pyrrolidino-pyridine, 4-dimethyl-amino-pyridine, quinoline, α-picoline, β-picoline, isoquinoline, pyrimidine, acridine, N,N,N',N'-tetramethylene-diamine, N,N',N'-tetraethylenediamine, quinoxaline, N-propyl-diisopropylamine, N-ethyl-diisopropylamine, N,N'-dimethyl-cyclohexylamine, 2,6-lutidine, 2,4-lutidine, triethylenediamine, diazabicyclooctane (DABCO), diazabicyclononene (DBN) or diazabicycloundecene (DBU).

Tertiary amines, in particular trialkylamines, such as triethylamine, N,N'-diisopropylethylamine or N-methyl-morpholine, are preferably used.

Suitable diluents for carrying out process 2 according to the invention are all inert organic solvents.

Examples which may be mentioned are: halogenohydrocarbons, in particular chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, dichlorobenzene, chlorotoluene, trichlorobenzene; alcohols, such as methanol, ethanol, isopropanol, butanol; ethers, such as ethyl propyl ether, methyl tert-butyl ether, n-butyl ether, di-n-butyl ether, di-isobutyl ether, diisoamyl ether, diisopropyl ether, anisole, phenetol, cyclohexyl methyl ether, diethyl ether, ethylene glycol dimethyl ether, tetrahydrofuran, dioxane, dichlorodiethyl ether; nitro hydrocarbons, such as nitromethane, nitroethane, nitrobenzene, chloronitrobenzene, o-nitrotoluene; nitriles, such as acetonitrile, butyronitrile, isobutyronitrile, benzonitrile, m-chlorobenzonitrile; aliphatic, cycloaliphatic or aromatic hydrocarbons, such as heptane, hexane, nonane, cymene, benzine fractions within a boiling point interval of 70° C. to 190° C., cyclohexane, methylcyclohexane, petroleum ether, ligroin, octane, benzene, toluene, xylene; esters, such as ethyl acetate, isobutyl acetate; amides, for example formamide, N-methylformamide, N,N-dimethylformamide, N-methyl-pyrrolidone; ketones, such as acetone, methyl ethyl ketone. Mixtures of the abovementioned solvents and diluents are also suitable.

Halogenohydrocarbons, in particular chlorohydrocarbons, such as methylene chloride and chloroform, or ethers, such as, for example, dioxane, and mixtures of alcohols and ethers, are preferred.

The hexadepsipeptides used as starting compounds can be prepared by traditional processes, for example the process described by H.-G. Lerchen and H. Kunz (Tetrahedron Lett. 26 (43) (1985) p. 5257–5260; 28 (17) (1987) p. 1873–1876) utilizing the esterification method described by B. F. Gisin (Helv. Chim. Acta 56 (1973) p. 1476).

The process is carried out by combining compounds of the formula (II) in the presence of one of the coupling reagents indicated and in the presence of a basic reaction auxiliary in a diluent under high dilution conditions and stirring the mixture. The reaction time is 4 to 72 hours. The reaction is carried out at temperatures between –5° C. and +100° C., preferably between –5° C. and +50° C., particularly preferably at 0° C. to room temperature. It is carried out under atmospheric pressure.

To carry out process 2 according to the invention, 1.0 to 3.0 mol, preferably 1.0 to 1.5 mol, of coupling reagent are generally employed per mole of N-methyl-L-alanyl-D-lactyl-N-methyl-L-isoleucyl-D-lactyl-N-methyl-L-isoleucyl-D-lactic acid of the formula II.

When the reaction has been completed, the reaction solution is washed until weakly alkaline, and the organic phase is separated off, dried and concentrated in vacuo. The products obtained can be purified in the customary manner by recrystallization or column chromatography (cf. also the Preparation Examples).

Process 2 allows cyclohexadepsipeptides to be obtained from open-chain hexadepsipeptides whose depsipeptide sequence is constructed in the L or D configuration, while retaining the original configuration of the starting materials.

Alternatively, the compounds of the formula (I) according to the invention can also be synthesized by the process used by U. Schmidt et al. for macrocyclic peptide alkaloids (cf. for example: U. Schmidt et al. in Synthesis (1991) p. 294–300 [didemnin A, B and C]; Angew. Chem. 96 (1984) p. 723–724 [dolastatin 3]; Angew. Chem. 102 (1990) p. 562–563 [fenestin A]; Angew. Chem. 97 (1985) p. 606–607 [ulicyclamid]; J. Org. Chem. 47 (1982) p. 3261–3264).

Some of the N-methyl-amino acids and 2-halogenocarboxylic acid derivatives used as starting materials are known (cf. for example: N-methyl-amino acids: R. Bowmann et al. J. Chem. Soc. (1950) p. 1346; J. R. McDermott et al. Can. J. Chem. 51 (1973) p. 1915; H. Wurziger et al., Kontakte [Catalysts] (Merck, Darmstadt) 3 (1987) p. 8; 2-halogenocarboxylic acid derivatives; S. M. Birnbaum et al. J. Amer. Chem. Soc. 76 (1954) p. 6054, C. S. Rondestvedt, Jr. et al. Org. Reactions 11 (1960) p. 189 [Review]) or can be obtained by the processes described in these publications.

Coupling reagents which can be used for the coupling reaction for synthesizing the depsipeptides (III), (IV), (V), (VI) and (VII) employed as starting compounds are all those which are suitable for producing amide linkage (cf. for example: Houben-Weyl, Methoden der organischen Chemie [Methods in Organic Chemistry], Vol. 15/2; Bodanszky et al., Peptide Synthesis 2nd ed. (Wiley & Sons, New York 1976) or Gross, Meienhofer, The Peptides: Analysis synthesis, biology (Academic Press, New York 1979).

In the case of the [L-D-L-D-L-D] isomer, for example, the open-chain hexadepsipeptides (II) can be obtained in a reaction sequence which embraces the following steps:

a) Synthesis of the [L-D]-configurated didepsipeptides of the formulae (Vi) to (VIIi):

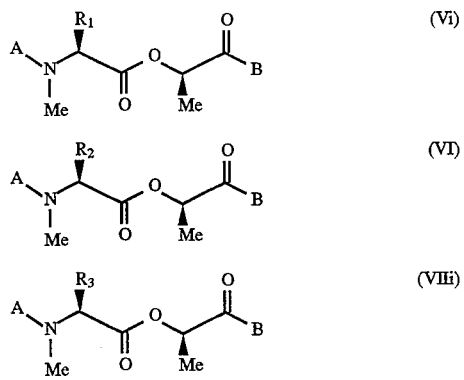

in which A is an N-terminal protective group, such as, for example, the benzyl or benzyloxycarbonyl group, and B is a C-terminal protective group, such as, for example, the tert-butoxy group.

In the case of formula (VIIa), in which B represents tert-butyloxy, this follows the equation:

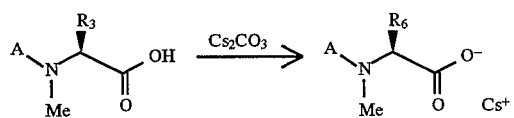

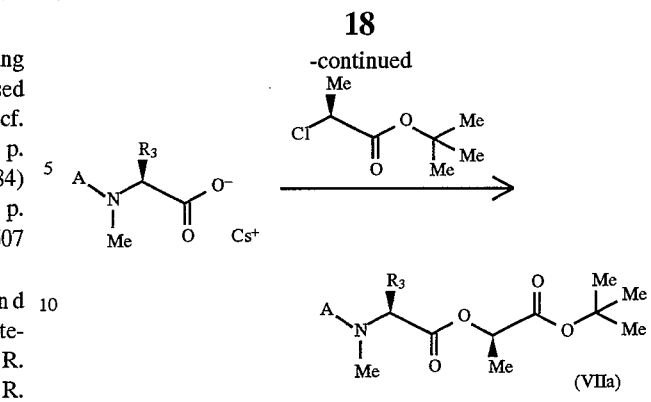

If appropriate, the preparation of the enantiomerically pure compounds of the formulae (V), (VI) and (VII) can be effected via separating the diastereomers by customary methods, such as, for example, crystallization, by column chromatography or by countercurrent distribution. The best possible process will have to be identified in each individual case; occasionally it is also advantageous to use combinations of the individual processes.

At the end of this step, it is possible either to remove the N-terminal protective group from the derivatives of the formula (VIIa) in a manner known per se, for example by catalytic hydrogenation, to prepare the derivatives of the formula (VIIc), or the C-terminal protective group can be eliminated from the derivatives of the formula (V) and (VI) in a manner known per se, preferably by acidolysis, to synthesize the derivatives (Vb) and (VIb):

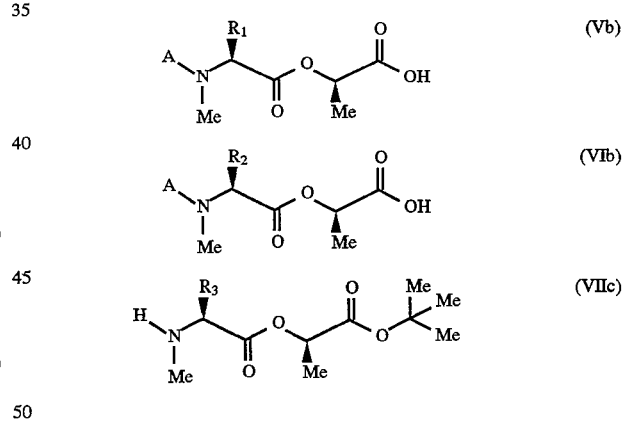

b) Synthesis of the [L-D-L-D]-configurated tetradepsipeptides of the formula (III-i) and (IVi)

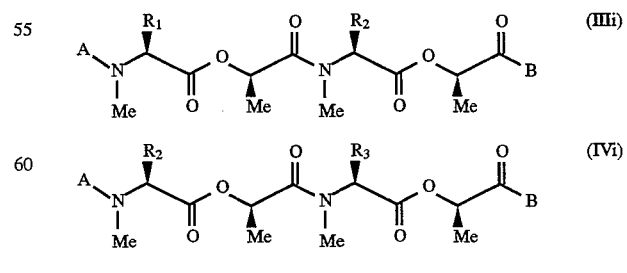

which, in the case of formula (IVa), for example, in which B represents tert-butyloxy, follows the equation:

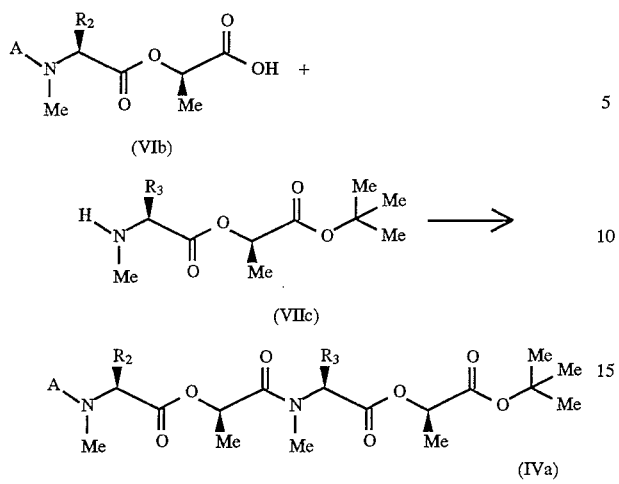

The N-terminal protective group can subsequently be eliminated from the derivatives of the formula (IVa), for example by catalytic hydrogenation as described above, to prepare the derivatives of the formula

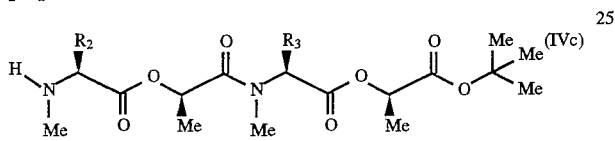

c) Synthesis of the open-chain [L-D-L-D-L-D]-configurated hexadepsipeptides of the formula

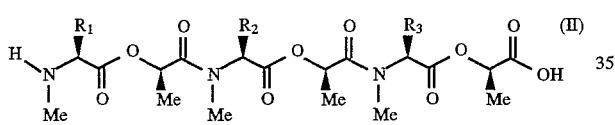

following the equation:

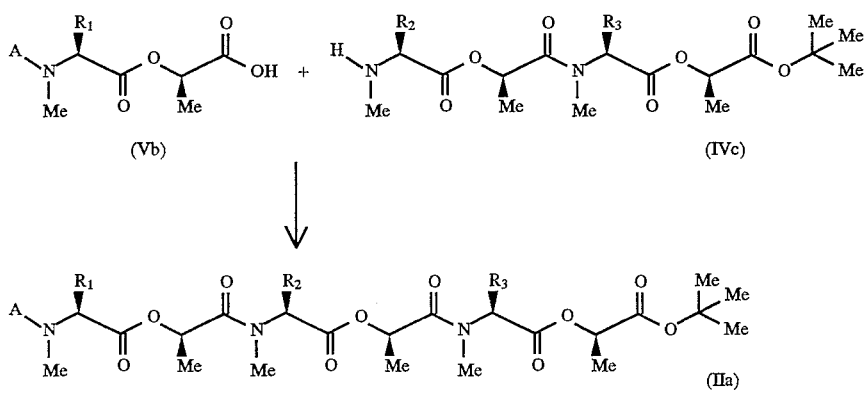

The C-terminal protective group can subsequently be eliminated from the derivatives of the formula (IIa) in a manner known per se, for example by acidolysis, to prepare the derivatives

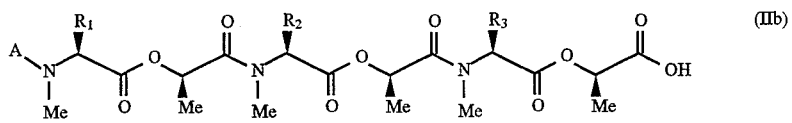 (IIb)

or the derivatives of the formula (IIa) are deblocked N-terminally in a manner known per se, for example by catalytic hydrogenation as described above, to prepare the derivatives of the formula

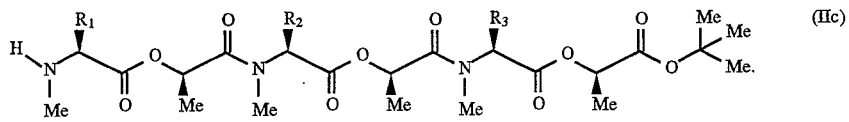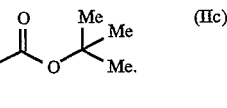 (IIc)

When these steps have been completed, the N-terminal or C-terminal protective group can be eliminated from the derivatives of the formula (IIb) or (IIc) in a manner known per se, for example by catalytic hydrogenation or by acidolysis, as described above, to prepare the derivatives of the formula

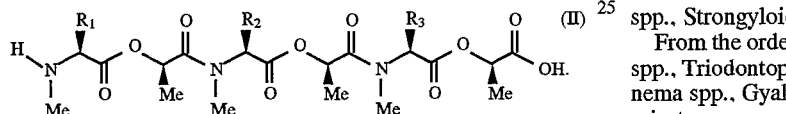 (II)

The products obtained can be purified in the customary manner by recrystallization or by column chromatography (cf. also the Preparation Examples).

While having low toxicity to warm-blooded species, the active compounds are suitable for combating pathogenic endoparasites which occur in humans and in animal keeping and livestock breeding, in productive livestock, breeding animals, zoo animals, laboratory animals, experimental animals and pets. In this context, they are active against all or individual stages of development of the pests and against resistant and normally-sensitive species. By combating the pathogenic endoparasites, it is intended to reduce disease, deaths and decreasing performance (for example in the production of meat, milk, wool, hides, eggs, honey etc.), so that more economical and simpler animal keeping is possible by using the active compounds. The pathogenic endoparasites include Cestodes, Trematodes, Nematodes and Acantocephala, in particular:

From the order of the Pseudophyllidea, for example: Diphyllobothrium spp., Spirometra spp., Schistocephalus spp., Ligula spp., Bothridium spp., Diphlogonoporus spp.

From the order of the Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example: Gyrodactylus spp., Dactylogyrus spp., Polystoma spp.

From the subclass of the Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridiumspp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoton spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonismus spp.

From the order of the Enoplida, for example: Trichuris spp., Capillaria spp., Trichomosoides spp., Trichinella spp.

From the order of the Rhabditia, for example: Micronema spp., Strongyloides spp.

From the order of the Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example: Oxyuris spp., Enterobius spp., Passalurus spp., Syphacia spp., Aspiculuris spp., Heterakis spp.

From the order of the Ascaridia, for example: Ascaris spp., Toxascaris spp., Toxocara spp., Parascaris spp., Anisakis spp., Ascaridia spp.

From the order of the Spirurida, for example: Gnathostoma spp., Physaloptera spp., Thelazia spp., Gongylonema spp., Habronema spp., Parabronema spp., Draschia spp., Dracunculus spp.

From the order of the Filariida, for example: Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example Filicollis spp., Moniliformis spp., Macracanthorhynchus spp., Prosthenorchis spp.

The productive livestock and breeding animals include mammals such as, for example, cattle, horses, sheep, pigs, goats, camels, water buffalo, donkeys, rabbits, fallow deer, reindeer, fur-bearing animals such as, for example, mink, chinchilla, racoon, birds such as, for example, chickens, geese, turkeys, ducks, freshwater and salt-water fish such as, for example, trout, carp, eels, reptiles, insects such as, for example, honeybee and silkworm.

Laboratory animals and experimental animals include mice, rats, guinea pigs, golden hamsters, dogs and cats.

Pets include dogs and cats.

Administration can be effected prophylactically as well as therapeutically.

The active compounds are administered, directly or in the form of suitable preparations, enterally, parenterally, dermally, nasally, by environment treatment, or with the aid of active-compound-containing shaped articles such as, for example, strips, plates, bands, collars, ear marks, limb bands, marking devices.

The active compounds are administered enterally, for example orally, in the form of powders, tablets, capsules, pastes, drinks, granules, or solutions, suspensions and emulsions which can be administered orally, or boli, medicated feed or drinking water. Dermal administration is effected, for example, in the form of dipping, spraying or pouring-on and spotting-on. Parenteral administration is effected, for example, in the form of injection (intramuscularly, subcutaneously, intravenously, intraperitoneally) or by implants.

Suitable preparations are:

Solutions such as injectable solutions, oral solutions, concentrates for oral administration after dilution, solutions for use on the skin or in body cavities, pour-on and spot-on formulations, gels;

Emulsions and suspension for oral or dermal administration and for injection; semi-solid preparations;

Formulations in which the active compound is incorporated in a cream base or in an oil-in-water or water-in-oil emulsion base;

Solid preparations such as powders, premixes or concentrates, granules, pellets, tablets, boli, capsules; aerosols and inhalants, shaped articles containing active compound.

Solutions for injection are administered intravenously, intramuscularly and subcutaneously.

Injectable solutions are prepared by dissolving the active compound in a suitable solvent and, if appropriate, adding additives such as solubilizers, acids, bases, buffer salts, antioxidants and preservatives. The solutions are sterile-filtered and drawn off.

The following may be mentioned as solvents: physiologically acceptable solvents such as water, alcohols such as ethanol, butanol, benzyl alcohol, glycerol, propylene glycol, polyethylene glycols, N-methyl-pyrrolidone, and mixtures of these.

If appropriate, the active compounds can also be dissolved in physiologically acceptable vegetable or synthetic oils which are suitable for injection.

The following may be mentioned as solubilizers: solvents which enhance solution of the active compound in the main solvent, or which prevent its precipitation. Examples are polyvinylpyrrolidone, polyoxyethylated castor oil, polyoxyethylated sorbitan esters.

Preservatives are: benzyl alcohol, trichlorobutanol, p-hydroxybenzoic esters, n-butanol.

Oral solutions are administered directly. Concentrates are administered orally after previously having been diluted to the administration concentration. Oral solutions and concentrates are prepared as described above in the case of the solutions for injection, it being possible to dispense with working under sterile conditions.

Solutions for use on the skin are applied dropwise, brushed on, rubbed in, splashed on or sprayed on. These solutions are prepared as described above in the case of solutions for injection.

It may be advantageous to add thickeners during the preparation. Thickeners are: inorganic thickeners such as bentonites, colloidal silica, aluminium monostearate, organic thickeners such as cellulose derivatives, polyvinyl alcohols and their copolymers, acrylates and methacrylates.

Gels are applied to, or brushed on, the skin, or introduced into body cavities. Gels are prepared by treating solutions which have been prepared as described in the case of the solutions for injection with such an amount of thickener that a clear substance of cream-like consistency is formed. Thickeners employed are the thickeners indicated further above.

Pour-on and spot-on formulations are poured onto, or splashed onto, limited areas of the skin, the active compound penetrating the skin and acting systemically.

Pour-on and spot-on formulations are prepared by dissolving, suspending or emulsifying the active compound in suitable solvents or solvent mixtures which are tolerated by the skin. If appropriate, other adjuvants such as colorants, resorption accelerators, antioxidants, light stabilizers, and tackifiers are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

Colorants are all colorants which are released for use on animals and which can be dissolved or suspended.

Examples of resorption accelerators are DMSO, spreading oils such as isopropyl myristate, dipropylene glycol pelargonate, silicone oils, fatty acid esters, triglycerides, fatty alcohols.

Antioxidants are sulphites or metabisulphites such as potassium metabisulphite, ascorbic acid, butylhydroxytoluene, butylhydroxyanisole, tocopherol.

Examples of light stabilizers are novantisolic acid.

Examples of tackifiers are cellulose derivatives, starch derivatives, polyacrylates, natural polymers such as alginates, gelatine.

Emulsions can be administered orally, dermally or in the form of injections.

Emulsions are either of the water-in-oil type or of the oil-in-water type.

They are prepared by dissolving the active compound either in the hydrophobic or in the hydrophilic phase and homogenizing this phase with the solvent of the other phase, with the aid of suitable emulsifiers and, if appropriate, other adjuvants such as colorants, resorption accelerators, preservatives, antioxidants, light stabilizers, viscosity-increasing substances.

The following may be mentioned as the hydrophobic phase (oils): paraffin oils, silicone oils, natural vegetable oils such as sesame seed oil, almond oil, castor oil, synthetic triglycerides such as caprylic/capric acid biglyceride, triglyceride mixture with vegetable fatty acids of chain length $C_{8-12}$ or with other specifically selected natural fatty acids, partial glyceride mixtures of saturated or unsaturated fatty acids which may also contain hydroxyl groups, and mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric esters of saturated fatty alcohols of chain length $C_{12}$-$C_{18}$, isopropyl stearate, oleyl oleate, decyl oleate, ethyl oleate, ethyl lactate, waxy fatty acid esters such as artificial uropygial gland fat from ducks, dibutyl phthalate, diisopropyl adipate, ester mixtures related to the latter, etc.

Fatty alcohols such as isotridecyl alcohol, 2-octyl dodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

The following may be mentioned as emulsifiers: non-ionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulphate, fatty alcohol ether sulphates, onoethynolamine salt of mono/dialkylpolyglycol ether orthophosphoric esters.

The following may be mentioned as other adjuvants: viscosity-increasing substances and substances which stabilize the emulsion, such as carboxymethylcellulose, methylcellulose and other cellulose and starch derivatives, polyacrylates, alginates, gelatine, gum arabic, polyvinyl pyrrolidone, polyvinyl alcohol, copolymers of methyl vinyl ether and maleic anhydride, polyethylene glycols, waxes, colloidal silica, or mixtures of the substances mentioned.

Suspensions can be administered orally, dermally or in the form of injection. They are prepared by suspending the active substance in an excipient liquid, if appropriate with the addition of further adjuvants such as wetting agents, colorants, resorption accelerators, preservatives, antioxidants light stabilizers.

Excipient liquids which may be mentioned are all homogeneous solvents and solvent mixtures.

Wetting agents (dispersants) which may be mentioned are the surfactants indicated further above.

Further adjuvants which may be mentioned are those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of adjuvants, and the mixture is formulated as desired.

Excipients which may be mentioned are all physiologically acceptable solid inert substances. Suitable as such are inorganic and organic substances. Examples of inorganic substances are sodium chloride, carbonates such as calcium carbonate, hydrogen carbonates, aluminium oxides, silicas, clays, precipitated or colloidal silica, and phosphates.

Examples of organic substances are sugars, cellulose, foods and animal feeds such as dried milk, carcass meals, cereal meals and coarse cereal meals and starches.

Adjuvants are preservatives, antioxidants and colorants which have already been indicated further above.

Other suitable adjuvants are lubricants and gliding agents such as, for example, magnesium stearate, stearic acid, talc, bentonites, disintegrants such as starch or crosslinked polyvinylpyrrolidone, binders such as, for example, starch, gelatine or linear polyvinylpyrrolidone, and also dry binders such as microcrystalline cellulose.

In the preparations, the active compounds can also be present in the form of a mixture with synergists or with other active compounds which act against pathogenic endoparasites. Examples of such active compounds are L-2,3,5,6-tetrahydro-6-phenylimidazothiazole, benzimidazole carbamates, praziquantel, pyrantel, febantel.

Ready-to-use preparations contain the active compound in concentrations from 10 ppm—20 percent by weight, preferably of from 0.1–10 percent by weight.

Preparations which are diluted prior to administration contain the active compound in concentrations of from 0.5–90 percent by weight, preferably from 5–50 percent by weight.

In general, it has proved advantageous to administer amounts of approximately 1 to approximately 100 mg of active compound per kg of body weight per day, to achieve effective results.

EXAMPLE A

In Vivo Nematode Test

*Trichostrongylus colubriformis*/Sheep

Sheep which have been infected experimentally with *Trichostrongylus colubriformis* were treated after the prepatent period had elapsed. The active compounds in the form of the pure active compound were administered orally and/or intravenously.

The degree of effectiveness is determined by quantitative determination of the nematode eggs excreted with the faeces before and after the treatment.

If, after the treatment, egg excretion stops completely, the nematodes were aborted or damaged to such an extent that they no longer produce eggs (dosis effectiva).

The table which follows shows active compounds which were tested and effective dosage rates (dosis effectiva).

| Active compound Example No. | Dosis effectiva in mg/kg |
| --- | --- |
| 1 | 10 |
| 2 | 10 |
| 5 | 10 |

EXAMPLE B

In Vivo Nematode Test

*Haemonchus contortus*/Sheep

Sheep which have been infected experimentally with *Haemonchus contortus* were treated after the prepatent period had elapsed. The active compounds in the form of the pure active compound were administered orally and/or intravenously.

The degree of effectiveness is determined by quantitative determination of the nematode eggs excreted with the faeces before and after the treatment.

If, after the treatment, egg excretion stops completely, the nematodes were aborted or damaged to such an extent that they no longer produce eggs (dosis effectiva).

The table which follows shows active compounds which were tested and effective dosage rates (dosis effectiva).

| Active compound Example No. | Dosis effectiva in mg/kg |
|---|---|
| 1 | 10 |
| 5 | 10 |
| 10 | 10 |
| 16 | 10 |

PREPARATIVE EXAMPLES

Example 1

Cyclo(-N-methyl-L-alanyl-D-lactyl-N-methyl-L-isoleucyl-D-lactyl-N-methyl-L-isoleucyl-D-lactyl-)

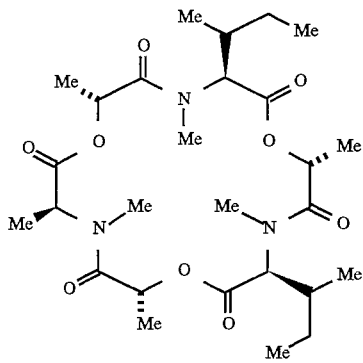

0.28 g (2.18 mmol) of N,N-diisopropylethylamine ("Hünig's Base") and 0.27 g (1.05 mmol) of bis(2-oxo-3-oxazolidinyl)phosphinic chloride (BOP-Cl) are added at 0° C. to a solution of 0.5 g (0.87 mmol) of N-methyl-L-alanyl-D-lactyl-N-methyl-L-isoleucyl-D-lactyl-N-methyl-L-isoleucyl-D-lactic acid in 500 ml of methylene chloride and the mixture is stirred for 24 hours at room temperature. Then, a further 0.28 g (2.18 mmol) of N,N-diisopropylethylamine ("Hünig's Base") and 0.27 g (1.05 mmol) of bis(2-oxo-3-oxazolidinyl)phosphinic chloride (BOP-Cl) are added at 0° C., and stirring is continued for 24 hours at room temperature. The reaction solution is washed twice with water, and the organic phase is separated off, dried over sodium sulphate and then concentrated in vacuo. The crude product which remains is chromatographed over a silica gel column (silica gel 60—Merck, mesh size: 0.04 to 0.063 mm) using toluene:ethyl acetate (2:1) as the eluent. 0.29 g (59.8% of theory, of cyclo(-N-methyl-L-alanyl-D-lactyl-N-methyl-L-isoleucyl-D-lactyl-N-methyl-L-isoleucyl-D-lactyl-) is obtained.

$^{13}$C-NMR (100 MHz, CDCl$_3$, δ): 10.6; 10.7; 13.5; 15.4; 15.9; 16.0; 16.8; 17.1 (—$\underline{C}$H$_3$); 24.4; 24.5 (—$\underline{C}$H$_2$—); 30.9; 31.5; (—$\underline{C}$H—); 32.8; 33.9; 34.2 (—N—$\underline{C}$H$_3$); 56.2; 59.9; 60.5 (—N—$\underline{C}$H—); 66.0; 66.3; 67.7 (—O—$\underline{C}$H—); 168.7; 169.7; 170.1 (—$\underline{C}$O—N—); 169.0; 170.0; 170.4 (—$\underline{C}$O—O—) ppm EI-MS m/z (%): 555 (M$^+$, 64); 499 (37); 483 (34); 428 (12); 357 (19); 340 (5); 255 (50); 182 (100); 100 (52).

The compounds of the formula (I) listed in Tables 1 to 4 below can be prepared analogously.

TABLE 1

Examples of compounds of the formula (I)

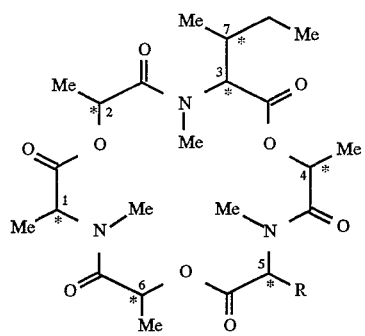

(I)

| Ex. No. | R radical | Configuration on* | | | | | | | Physical data[a)] |
|---|---|---|---|---|---|---|---|---|---|
| | | C-1 | C-2 | C-3 | C-4 | C-5 | C-6 | C-7 | |
| 2 | —H | L | D | L | D | — | D | L | 499 (M$^+$, 100); 428 (38); 312 (28); 213 (62); 182 (73); 140 (49) |
| 3 | —H | L | D | L | D | — | D | D | |
| 4 | —H | D | L | D | L | — | L | D | |
| 5 | —CH$_3$ | L | D | L | D | L | D | L | 31.8; 33.8; 34.6 (—N—$\underline{C}$H$_3$); 168.1; 168.7; 169.9; (—$\underline{C}$O—N—) 170.0; 170.4; 170.5 (—$\underline{C}$O—O—); 513 (M$^+$, 42); 440 (22); 255 (29); 213 (60); 182 (75); 141 (82); 58 (100) |
| 6 | —C$_2$H$_5$ | L | D | L | D | L | D | L | 527 (M$^+$, 100); 472 (27); 454 (42); 255 (36); 182 (92) |
| 7 | -n-C$_3$H$_7$ | L | D | L | D | L | D | L | 30.1; 33.9; 34.8 (—N—$\underline{C}$H$_3$); 168.6; 168.7; 169.9 (—$\underline{C}$O—N—); 170.0; 170.3; 170.4 (—$\underline{C}$O—O—); |

TABLE 1-continued

Examples of compounds of the formula (I)

[Structure (I): cyclic depsipeptide with positions labeled 1-7, substituent R at position 5]

| Ex. No. | R radical | Configuration on* C-1 | C-2 | C-3 | C-4 | C-5 | C-6 | C-7 | Physical data[a] |
|---|---|---|---|---|---|---|---|---|---|
| 8 | -n-$C_3H_7$ | L | D | L | D | L | D | D | 541 ($M^+$, 87); 468 (41); 354 (18); 255 (42); 213 (41); 182 (100); 141 (90) |
| 9 | -n-$C_3H_7$ | D | L | D | L | D | L | D | |
| 10 | -i-$C_3H_7$ | L | D | L | D | L | D | L | 30.9; 31.2; 33.9 ($-N-\underline{C}H_3$); 168.5; 168.6; 169.7 ($-\underline{C}O-N-$); 169.9; 170.1; 170.4 ($-\underline{C}O-O-$) |
| 11 | -i-$C_3H_7$ | L | D | L | D | L | D | D | 541 ($M^+$, 81); 468 (39); 255 (49); 213 (36); 182 (100); 141 (68) |
| 12 | -i-$C_3H_7$ | D | L | D | L | D | L | D | |
| 13 | -n-$C_4H_9$ | L | D | L | D | L | D | L | |
| 14 | -n-$C_4H_9$ | L | D | L | D | L | D | D | |
| 15 | -n-$C_4H_9$ | D | L | D | L | D | L | D | |
| 16 | -i-$C_4H_9$ | L | D | L | D | L | D | L | 29.9; 33.9; 34.9 ($-N-\underline{C}H_3$); 168.4; 168.7; 169.9 ($-\underline{C}O-N-$); 170.0; 170.3; 170.5 ($-\underline{C}O-O-$); |
| 17 | -i-$C_4H_9$ | L | D | L | D | L | D | D | 555 ($M^+$, 45); 499 (49); 428 (12); 255 (40); 182 (100); 141 (42) |
| 18 | -i-$C_4H_9$ | D | L | D | L | D | L | D | |

[a] $^{13}$C-NMR (100 MHz; $CDCl_3$, δ) [in ppm]; FAB-MS or EI-MS m/z (%)

TABLE 2

Examples of compounds of the formula (Ia, R: -methyl)

[Structure (Ia)]

| Ex. No. | Configuration on* C-1 | C-2 | C-3 | C-4 | C-5 | C-6 | C-7 |
|---|---|---|---|---|---|---|---|
| 19 | L | D | L | D | L | D | D |
| 20 | L | D | D | D | L | D | L |
| 21 | D | L | D | D | D | L | L |
| 22 | L | D | L | L | L | D | L |
| 23 | L | D | D | L | L | D | L |
| 24 | D | L | L | L | D | L | L |
| 25 | D | L | L | D | D | L | L |
| 26 | D | L | D | L | D | L | L |
| 27 | D | L | D | L | D | L | D |

TABLE 3

Examples of compounds of the formula (Ib, R: -ethyl)

(Ib)

| Ex. No. | Configuration on* | | | | | | |
|---|---|---|---|---|---|---|---|
| | C-1 | C-2 | C-3 | C-4 | C-5 | C-6 | C-7 |
| 28 | L | D | L | D | L | D | D |
| 29 | L | D | D | D | L | D | L |
| 30 | D | L | D | D | D | L | L |
| 31 | L | D | L | L | L | D | L |
| 32 | L | D | D | L | L | D | L |
| 33 | D | L | L | L | D | L | L |
| 34 | D | L | L | D | D | L | L |
| 35 | D | L | D | L | D | L | L |
| 36 | D | L | D | L | D | L | D |

TABLE 4

Examples of compounds of the formula (Ic, R: -sec-butyl)

(Ic)

| Ex. No. | Configuration on* | | | | | | | |
|---|---|---|---|---|---|---|---|---|
| | C-1 | C-2 | C-3 | C-4 | C-5 | C-6 | C-7 | C-8 |
| 37 | L | D | L | D | L | D | L | D |
| 38 | L | D | L | D | L | D | D | D |
| 39 | L | D | L | D | L | D | D | L |
| 40 | L | D | D | D | L | D | L | L |
| 41 | D | L | D | D | L | D | L | L |
| 42 | L | D | L | L | L | D | L | L |
| 43 | L | D | D | L | L | D | L | L |
| 44 | D | L | L | D | L | D | L | L |
| 45 | D | L | L | D | D | L | L | L |
| 46 | D | L | D | L | D | L | L | L |
| 47 | D | L | D | L | D | L | D | D |
| 48 | D | L | D | L | D | L | L | D |
| 49 | D | L | D | L | D | L | D | L |

Starting Substances of the Formula (II)

Example (II-1)

tert-Butyl N-benzyloxycarbonyl-N-methyl-L-alanyl-D-lactyl-N-methyl-L-isoleucyl-D-lactyl-N-methyl-L-isoleucyl-D-lactate

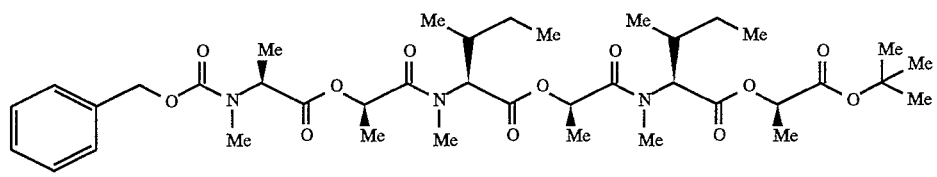

4.6 g (35.6 mmol) of N,N-diisopropylethylamine ("Hünig's Base) and 4.5 g (17.8 mmol) of bis(2-oxo-3-oxazolidinyl)phosphinic chloride (BOP-Cl) are added at 0°

C. to a solution of 5.0 g (16.2 mmol) of N-benzyloxycarbonyl-N-methyl-L-alanyl-D-lactic acid and 7.6 g (16.2 mmol) of tert-butyl N-methyl-L-isoleucyl-D-lactyl-N-methyl-L-isoleucyl-D-lactate in 200 ml of methylene chloride and the mixture is stirred for 4 hours at room temperature. The reaction solution is washed twice with water and the organic phase is separated off, dried over sodium sulphate and then concentrated in vacuo. The crude product which remains is chromatographed over a silica gel column (silica gel 60—Merck, mesh size: 0.04 to 0.063 mm) using toluene:ethyl acetate (3:1) as the eluent.

7.4 g (59.9% of theory) of tert-butyl N-benzyloxycarbonyl -N-methyl-L-alanyl-D-lactyl-N-methyl-L-isoleucyl-D-lactyl-N-methyl-L-isoleucyl-D-lactate are obtained.

EI-MS m/z (%): 763 ($M^+$, 10); 707 ($M^+$—$CH_2$=$CMe_2$, 12); 690 ($M^+$—$OCMe_3$, 7); 651 (9); 491 (19); 419 (34); 386 (24); 292 (25); 183 (41); 148 (42); 91 (Ph—$CH_2$, 100).

EI-MS m/z (%): 719 ($M^+$,45); 646 (50); 600 (80); 544 (82); 148 (100).

Example (II-3)

N-Benzyloxycarbonyl-N-methyl-L-alanyl-D-lactyl-N-methyl-L-isoleucyl-D-lactyl-N-methyl-L-isoleucyl-D-lactic acid

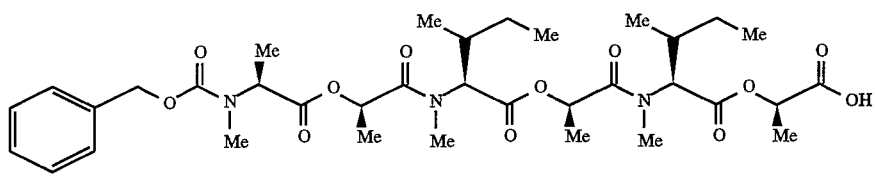

Example (II-2)
tert-Butyl N-benzyl-N-methyl-L-alanyl-D-lactyl-N-methyl-L-isoleucyl-D-lactyl-N-methyl-L-isoleucyl-D-lactate Dry hydrogen chloride gas is passed for 20 minutes into a solution of 6.2 g (8.12 mmol) of tert-butyl N-benzyloxycarbonyl-N-methyl-L-alanyl-D-lactyl-N-methyl-L-isoleucyl-D-lactyl-N-methyl-L-isoleucyl-D-lactate in 220 ml of absolute methylene chloride, cooled to 0° C. The mixture is subsequently stirred for approximately 16 hours at room temperature, and the entire reaction batch is concentrated in vacuo.

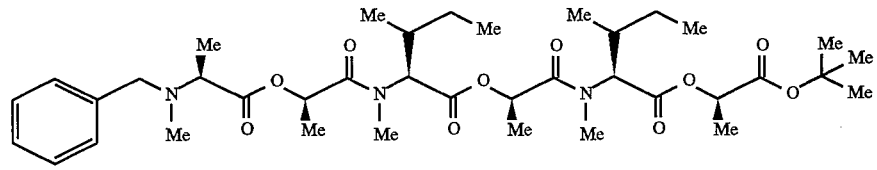

The coupling reaction is carried out analogously to the reaction protocol of Example (II-1) using:

14.0 g (52.9 mmol) of N-benzyl-N-methyl-L-alanyl-D-lactic acid,
25.0 g (52.9 mmol) of tert-butyl N-methyl-L-isoleucyl-D-lactyl-N-methyl-L-isoleucyl-D-lactate,
500 ml of methylene chloride,
15.0 g (116.3 mmol) of N,N-diisopropylethylamine ("Hünig's Base") and
14.8 g (58.2 mmol) of bis(2-oxo-3-oxazolidinyl) phosphinic chloride (BOP-Cl).

The crude product which remains is chromatographed over a silica gel column (silica gel 60—Merck, mesh size: 0.04 to 0.063 mm) using cyclohexane:ethyl acetate (1:1) as the eluent. 22.0 g (57.8% of theory) of tert-butyl N-benzyl-N-methyl-L-alanyl-D-lactyl-N-methyl-L-isoleucyl-D-lactyl-N-methyl-L-isoleucyl-D-lactate are obtained.

4.9 g (85.3% of theory) of N-benzyloxycarbonyl-N-methyl-L-alanyl-D-lactyl-N-methyl-L-isoleucyl-D-lactyl-N-methyl-L-isoleucyl-D-lactic acid are obtained, and this can be reacted further without further purification.

MS m/z (%): 708 ($M^+$+H, 1); 707 ($M^+$, 6); 651 (3); 572 (1); 436 (3); 292 (3); 192 (8); 148 (30); 91 (Ph—$CH_2$, 100).

Example (II-4)

N-Benzyl-N-methyl-L-alanyl-D-lactyl-N-methyl-L-isoleucyl-D-lactyl-N-methyl-L-isoleucyl-D-lactic acid

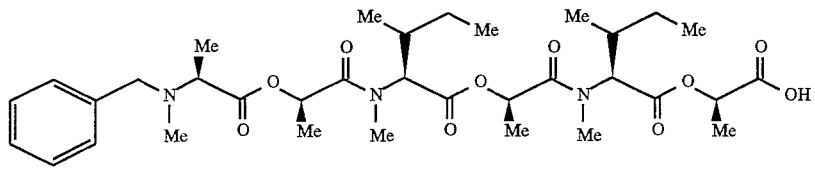

C-terminal acidolysis is carried out analogously to the reaction protocol of Example (II-3) using:

21.8 g (30.3 mmol) of tert-butyl N-benzyl-N-methyl-L-alanyl-D-lactyl-N-methyl-L-isoleucyl-D-lactyl-N-methyl-L-isoleucyl-D-lactate and 500 ml of methylene chloride.

20.0 g (99.5% of theory) of N-benzyl-N-methyl-L-alanyl-D-lactyl-N-methyl-L-isoleucyl-D-lactyl-N-methyl-L-isoleucyl-D-lactic acid are obtained, and this can be reacted further without further purification.

FAB-MS m/z (%): 665 ($M^+$+H, 37); 664 ($M^+$,100); 148 (82).

Example (II-5)

N-Methyl-L-alanyl-D-lactyl-N-methyl-L-isoleucyl-D-lactyl-N-methyl-L-isoleucyl-D-lactic acid

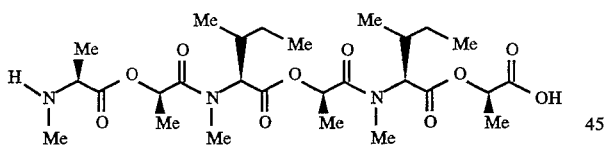

4.5 g (6.36 mmol) of N-benzyloxycarbonyl-N-methyl-L-alanyl-D-lactyl-N-methyl-L-isoleucyl-D-lactyl-N-methyl-L-isoleucyl-D-lactic acid are hydrogenated in 180 ml of ethanol in the presence of 0.45 g of Pd(OH)$_2$/charcoal [Pd content: 20%] until hydrogen is no longer taken up (approximately 4 hours). After the catalyst has been filtered off, the entire reaction solution is concentrated in vacuo.

3.6 g (98.7% of theory) of N-methyl-L-alanyl-D-lactyl-N-methyl-L-isoleucyl-D-lactyl-N-methyl-L-isoleucyl-D-lactic acid are obtained, and this can be cyclized without further purification.

EI-MS m/z (%): 573 ($M^+$,2); 472 (14); 386 (34); 285 (17); 183 (82); 155 (27); 100 (60); 58 (MeNH—CHMe, 100).

The synthesis of:

Example (II-6)

N-Methyl-L-isoleucyl-D-lactyl-N-methyl-L-alanyl-D-lactyl-N-methyl-L-isoleucyl-D-lactic acid

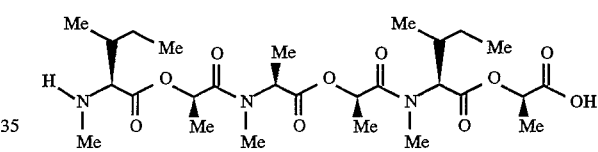

and

Example (II-7)

N-Methyl-L-isoleucyl-D-lactyl-N-methyl-L-isoleucyl-D-lactyl-N-methyl-L-alanyl-D-lactic acid

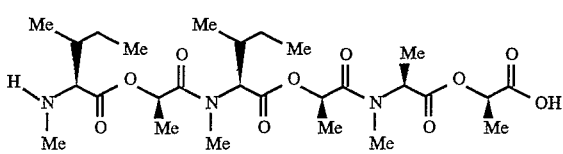

is carried out analogously to the reaction protocol of Example (II-5).

The starting substances of the general formula (II) listed in Table 5 below can be prepared analogously in the form of the [L-D-L-D-L-D]-stereoisomers:

TABLE 5

Examples of starting substances of the general formula (IIi)

$$\text{A-N(Me)-CHR}_1\text{-CO-O-CH(Me)-CO-N(Me)-CHR}_2\text{-CO-O-CH(Me)-CO-N(Me)-CHR}_3\text{-CO-O-CH(Me)-CO-B} \quad \text{(IIi)}$$

| Ex No. | A | R¹ | R² | R³ | B | Physical data[a] |
|---|---|---|---|---|---|---|
| II-8 | —Z | —H | —CH₃ | -s-C₄H₉ | —O-t-C₄H₉ | 707 (M⁺, 7); 650 (M⁺ —CMe₃, 15); 435 (15); 91 (100) 363 |
| II-9 | —Z | —H | —CH₃ | -s-C₄H₉ | —OH | 652 (M⁺ + H, 24); 608 (3); 363 (24); 91 (100) |
| II-10 | —H | —H | —CH₃ | -s-C₄H₉ | —OH | 517 (M⁺, 4); 461 (2); 141 (100) |
| II-11 | —Bn | —CH₃ | —CH₃ | -s-C₄H₉ | —O-t-C₄H₉ | 677 (M⁺, 2); 620 (M⁺ —OCMe₃, 5); 558 (2); 502 (2); 190 (100) |
| II-12 | —Bn | —CH₃ | -s-C₄H₉ | —CH₃ | —O-t-C₄H₉ | |
| II-13 | —Bn | -s-C₄H₉ | —CH₃ | —CH₃ | —O-t-C₄H₉ | |
| II-14 | —Bn | —CH₃ | —CH₃ | -s-C₄H₉ | —OH | 621 (M⁺, 2); 564 (2), 502 (3); 335 (5); 190.(100) |
| II-15 | —Bn | —CH₃ | -s-C₄H₉ | —CH₃ | —OH | |
| II-16 | —Bn | -s-C₄H₉ | —CH₃ | —CH₃ | —OH | |
| II-17 | —H | —CH₃ | —CH₃ | -s-C₄H₉ | —OH | 531 (M⁺, 6); 487 (12), 474 (42); 388 (80) |
| II-18 | —H | —CH₃ | -s-C₄H₉ | —CH₃ | —OH | |
| II-19 | —H | -s-C₄H₉ | —CH₃ | —CH₃ | —OH | |
| II-20 | —Z | -C₂H₅ | —CH₃ | —CH₃ | —O-t-C₄H₉ | 735 (M⁺, 13); 679 (M⁺, —H₂C=CMe₂) |
| II-21 | —Z | -C₂H₅ | —CH₃ | —CH₃ | —OH | 679 (M⁺, 10); 91 (100) |
| II-22 | —H | -C₂H₅ | —CH₃ | —CH₃ | —OH | 546 (M⁺, H, 10); 512 (14) |
| II-23 | —Bn | -n-C₃H₇ | —CH₃ | -s-C₄H₉ | —O-t-C₄H₉ | 705 (M⁺, 2); 632 (M⁺ —OCMe₃, 2); 586 (3); 530 (3); 176 (100) |
| II-24 | —Bn | -n-C₃H₇ | —CH₃ | -s-C₄H₉ | —OH | 649 (M⁺, 1); 530 (4); 176 (100) |
| II-25 | —H | -n-C₃H₇ | —CH₃ | -s-C₄H₉ | —OH | 539 (M⁺, 1); 86 (100) |
| II-26 | —Bn | -i-C₃H₇ | —CH₃ | -s-C₄H₉ | —O-t-C₄H₉ | 705 (M⁺, 2); 632 (M⁺ —OCMe₃; 3); 586 (5); 530 (7); 176 (100) |
| II-27 | —Bn | -i-C₃H₇ | —CH₃ | -s-C₄H₉ | —OH | 649 (M⁺, 2); 606 (4); 530 (8); 176 (100) |
| II-28 | —H | -i-C₃H₇ | —CH₃ | -s-C₄H₉ | —OH | 539 (M⁺, 0.5); 516 (5) |
| II-29 | —Z | -i-C₄H₉ | —CH₃ | -s-C₄H₉ | —O-t-C₄H₉ | 763 (M⁺, 2) ; 190 (48); 91 (100) |
| II-30 | —Z | -i-C₄H₉ | —CH₃ | -s-C₄H₉ | —OH | 707 (M⁺, 1); 651 (2); 419 (5); 91 (100) |
| II-31 | —H | -i-C₄H₉ | —CH₃ | -s-C₄H₉ | —OH | 573 (M⁺, 0.5); 100 (100) |

[a] FAB-MS or EI-MS m/z (%); Z: —CO—O—CH₂-phenyl; Bn: —CH₂-phenyl

Starting Substances of the Formula (III)

Example (III-1)

tert-Butyl N-benzyl-N-methyl-L-isoleucyl-D-lactyl-N-methyl-L-isoleucyl-D-lactate

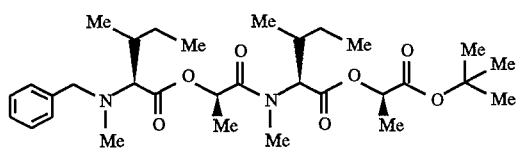

The coupling reaction is carried out analogously to the reaction the protocol of Example (II-1) using:

20.4 g (66.6 mmol) of N-benzyl-N-methyl-L-isoleucyl-D-lactic acid, 18.2 g (66.6 mmol) of tert-butyl N-methyl-L-isoleucyl-D-lactate, 500 ml of methylene chloride, 18.9 g (146.4 mmol) of N,N-diisopropylethylamine ("Hünig's Base") and 18.6 g (73.2 mmol) of bis(2-oxo-3-oxazolidinyl)-phosphinic chloride (BOP-Cl).

37.0 g (98.8% of theory) of tert-butyl N-benzyl-N-methyl-L-isoleucyl-D-lactyl-N-methyl-L-isoleucyl-D-lactate are obtained, and this can be reacted further without further purification.

EI-MS m/z (%): 563 (M⁺+H, 1); 562 (M⁺, 3); 505 (M⁺—CMe₃, 7); 489 (M⁺—OCMe₃, 6); 190 (100).

Example (III-2)

tert-Butyl N-benzyl-N-methyl-L-alanyl-D-lactyl-N-methyl-L-isoleucyl-D-lactate

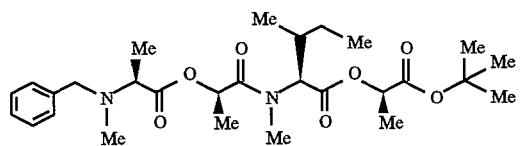

The coupling reaction is carried out analogously to the reaction protocol of Example (II-1) using:

13.6 g (51.3 mmol) of N-benzyl-N-methyl-L-alanyl-D-lactic acid, 14.0 g (51.3 mmol) of tert-butyl N-methyl-L-isoleucyl-D-lactate, 300 ml of methylene chloride, 14.6 g (112.7 mmol) of N,N-diisopropylethylamine ("Hünig's Base") and 14.4 g (56.4 mmol) of bis(2-oxo-3-oxazolidinyl)-phosphinic chloride (BOP-Cl).

26.7 g (100% of theory) of tert-butyl N-benzyl-N-methyl-L-alanyl-D-lactyl-N-methyl-L-isoleucyl-D-lactate are obtained, and this can be reacted further without further purification.

EI-MS m/z (%): 520 ($M^+$,46); 447 ($M^+$—$OCMe_3$, 77); 345 (42); 148 (100).

Example (III -3)

tert-Butyl N-benzyl-N-methyl-L-isoleucyl-D-lactyl-N-methyl-L-alanyl-D-lactate

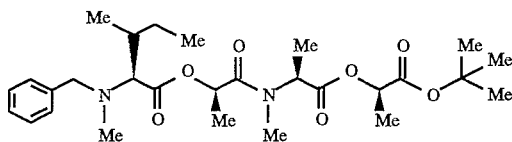

The coupling reaction is carried out analogously to the reaction protocol of Example (II-1) using:

5.0 g (16.3 mmol) of N-benzyl-N-methyl-L-isoleucyl-D-lactic acid, 3.7 g (16.3 mmol) of tert-butyl N-methyl-L-alanyl-D-lactate, 150 ml of methylene chloride, 4.6 g (35.7 mmol) of N,N-diisopropylethylamine ("Hünig's Base") and 4.6g (17.9 mmol) of bis(2-oxo-3-oxazolidinyl)-phosphinic chloride (BOP-Cl).

The crude product which remains is chromatographed over a silica gel column (silica gel 60—Merck, mesh size: 0.04 to 0.063 mm) using cyclohexane:ethyl acetate (6:1) as the eluent. 5.1 g (60.4% of theory) of tert-butyl N-benzyl-N-methyl-L-isoleucyl-D-lactyl-N-methyl-L-alanyl-D-lactate are obtained.

EI-MS m/z (%): 520 ($M^+$, 58); 463 ($M^+$—$CMe_3$, 76); 447 ($M^+$—$OCMe_3$, 91); 190 (100).

Example (III-4)

tert-Butyl N-benzyl-N-methyl-L-alanyl-D-lactyl-N-methyl-L-alanyl-D-lactate

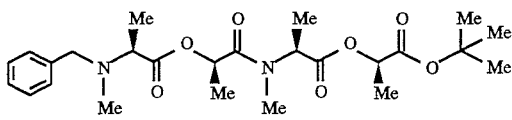

The coupling reaction is carried out analogously to the reaction protocol of Example (II-1) using:

24.8 g (93.3 mmol) of N-benzyl-N-methyl-L-alanyl-D-lactic acid, 21.4 g (93.3 mmol) of tert-butyl N-methyl-L-alanyl-D-lactate, 500 ml of methylene chloride, 26.5 g (205.1 mmol) of N,N-diisopropylethylamine ("Hünig's Base") and 26.1 g (102.6 mmol) of bis(2-oxo-3-oxazolidinyl)-phosphinic chloride (BOP-Cl).

The crude product which remains is chromatographed over a silica gel column (silica gel 60—Merck, mesh size: 0.04 to 0.063 mm) using cyclohexane:ethyl acetate (2:1) as the eluent. 16.5 g (36.9% of theory) of tert-butyl N-benzyl-N-methyl-L-alanyl-D-lactyl-N-methyl-L-alanyl-D-lactate are obtained.

EI-MS m/z (%): 478 ($M^+$,1); 405 ($M^+$—$OCMe_3$, 6); 148 (100).

Example (III-5)

tert-Butyl N-benzyl-N-methyl-L-isoleucyl-D-lactyl-N-methyl-L-isoleucyl-D-lactate

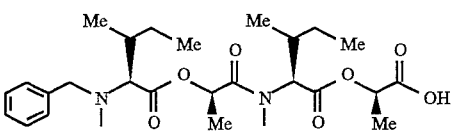

C-terminal acidolysis is carried out analogously to the reaction protocol of Example (II-3) using:

9.0 g (15.9 mmol) of tert-butyl N-benzyl-N-methyl-L-isoleucyl-D-lactyl-N-methyl-L-isoleucyl-D-lactate and 300 ml of methylene chloride.

8.2 g (100% of theory) of N-benzyl-N-methyl-L-isoleucyl-D-lactic acid are obtained, and this can be reacted further without further purification.

EI-MS m/z (%): 506 ($M^+$,2); 449 (8); 190 (100).

Starting Substances of the Formula (IV)

Example (IV-1)

tert-Butyl N-methyl-L-isoleucyl-D-lactyl-N-methyl-L-isoleucyl-D-lactate

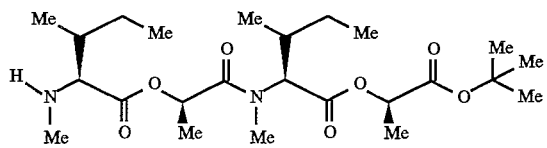

N-terminal deblocking is carried out analogously to the reaction protocol of Example (II-5) in the course of approximately 4 hours using:

35.0 g (62.2 mmol) of tert-butyl N-benzyloxycarbonyl-N-methyl-L-isoleucinyl-D-lactyl-N-methyl-L-isoleucyl-D-lactate, 3.5 g of Pd(OH)$_2$/charcoal [Pd content: 20%] and 700 ml of ethanol.

25.1 g (85.4% of theory) of tert-butyl N-methyl-L-isoleucyl-D-lactyl-N-methyl-L-isoleucyl-D-lactate are obtained, and this can be used for the coupling reaction without further purification.

EI-MS m/z (%): 472 ($M^+$,6); 359 (6); 273 (6); 100 (100).

Example (IV-2)

tert-Butyl N-methyl-L-alanyl-D-lactyl-N-methyl-L-isoleucyl-D-lactate

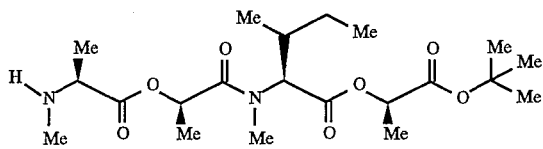

N-terminal deblocking is carried out analogously to the reaction protocol of Example (II-5) in the course of approximately 4 hours using:

26.3 g (50.5 mmol) of tert-butyl N-benzyl-N-methyl-L-alanyl-D-lactyl-N-methyl-L-isoleucyl-D-lactate, 30.0 g of Pd(OH)$_2$/charcoal [Pd content: 20%] and 500 ml of ethanol.

21.3 g (98.0% of theory) of tert-butyl N-methyl-L-alanyl-D-lactyl-N-methyl-L-isoleucyl-D-lactate are obtained, and this can be used for the coupling reaction without further purification.

Example (IV-3)

tert-Butyl N-methyl-L-isoleucyl-D-lactyl-N-methyl-L-alanyl-D-lactate

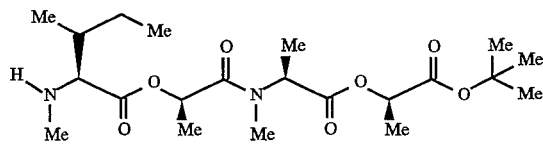

N-terminal deblocking is carried out analogously to the reaction protocol of Example (II-5) in the course of approximately 4 hours using:

4.8 g (9.3 mmol) of tert-butyl N-benzyl-N-methyl-L-isoleucyl-D-lactyl-N-methyl-L-alanyl-D-lactate, 0.5 g of Pd(OH)$_2$/charcoal [Pd content: 20%] and 100 ml of ethanol.

3.2 g (83.2% of theory) of tert-butyl N-methyl-L-isoleucyl-D-lactyl-N-methyl-L-alanyl-D-lactate are obtained, and this can be used for the coupling reaction without further purification.

FAB-MS m/z (%): 431 (M$^+$+H, 12); 190 (100).

Example (IV-4)

tert-Butyl N-methyl-L-alanyl-D-lactyl-N-methyl-L-alanyl-D-lactate

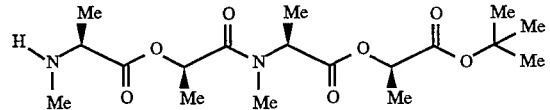

N-terminal deblocking is carried out analogously to the reaction protocol of Example (II-5) in the course of approximately 4 hours using:

15.0 g (32.0 mmol) of tert-butyl N-benzyl-N-methyl-L-alanyl-D-lactyl-N-methyl-L-alanyl-D-lactate, 1.5 g of Pd(OH)$_2$/charcoal [Pd content: 20%] and 400 ml of ethanol.

10.8 g (89.5% of theory) of tert-butyl N-methyl-L-alanyl-D-lactyl-N-methyl-L-alanyl-D-lactate are obtained, and this can be used for the coupling reaction without further purification.

FAB-MS m/z (%): 388 (M$^+$,0.5); 344 (M$^+$—CO$_2$, 4); 315 (15); 58 (100).

Starting Substances of the Formula (V), (VI) and (VII)

Example (V-1)

tert-Butyl N-benzyl-N-methyl-L-alanyl-D-lactate

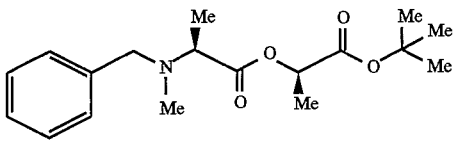

7.0 g (36.2 mmol) of N-benzyl-N-methyl-L-alanine are dissolved in 155 ml of methanol and 15 ml of water, 30 ml of a 20% strength caesium carbonate solution are added, and the mixture is stirred for approximately one hour at room temperature. This is subsequently treated three times with approximately 100 ml of absolute dimethylformamide, concentrated in vacuo and dried under a high vacuum. The caesium salt is introduced in 76 ml of dimethylformamide, 6.0 g (36.2 mmol) of tert-butyl L-2-chloro-lactate are added, and the mixture is stirred at room temperature for approximately 18 hours.

The entire reaction solution is concentrated in vacuo, the oily residue is taken up in methylene chloride, and the mixture is shaken twice with water. The organic phase is then separated off, dried over sodium sulphate and concentrated in vacuo.

8.9 g (76.5% of theory) of tert-butyl N-benzyl-N-methyl-L-alanyl-D-lactate are obtained, and this can be reacted further without further purification.

$^1$H-NMR (400 MHz, CDCl$_3$, δ): 1.37; 1.49 (2d, 6H, 2×—CH$_3$; J=7.1 Hz); 1.47 (s, 9H, —OCMe$_3$); 2.34 (s, 3H, —N—CH$_3$); 3.51 (q, 1H, —O—CH—; J=7.1 Hz); 3.74 (dd, 2H, Ph—CH$_2$—); 4.97 (q, 1H, —N—CH—; J=7.1 Hz); 7.23–7.37 (m, 5H, aromatic H) ppm EI-MS m/z (%): 321 (M$^+$,1); 248 (2); 148 (Ph—CH$_2$—NMe—CHMe, 100); 91 (Ph—CH$_2$, 63).

Example (VI-1)

N-Benzyl-N-methyl-L-isoleucyl-D-lactic acid

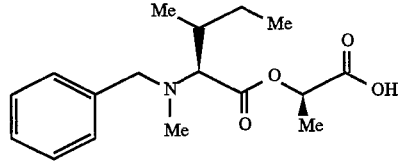

C-terminal acidolysis is carried out analogously to the reaction protocol of Example (II-3) using:

25.0 g (68.8 mmol) of tert-butyl N-benzyl-N-methyl-L-isoleucyl-D-lactate and 500 ml of methylene chloride.

21.0 g (99.3% of theory) of N-benzyl-N-methyl-L-isoleucyl-D-lactic acid are obtained, and this can be reacted further without further purification.

EI-MS m/z (%): 307 (M⁺, 3); 250 (28); 190 (PhCH₂—NMe—CH—CHMeCH₂Me, 100); 91 (PhCH₂, 85).

Example (VII-1)

tert-Butyl N-methyl-L-isoleucyl-D-lactate

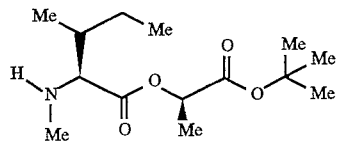

N-terminal deblocking is carried out analogously to the reaction protocol of Example (II-5) using:

- 25.0 g (68.8 mmol) of tert-butyl N-benzyl-N-methyl-L-isoleucyl-D-lactate,
- 500 ml of ethanol and
- 2.5 g of Pd(OH)₂/charcoal [Pd content: 20%].

18.2 g (96.8% of theory) of tert-butyl N-methyl-L-isoleucyl-D-lactate are obtained, and this can be reacted further without further purification.

¹H-NMR (400 MHz, CDCl₃, δ): 1.47 (s, 9H, 3×CH₃); 2.40 (s, 3H, —N—CH₃) ppm.

The compounds of formulae (V)—(VII) listed in Tables 6 to 8 below can be prepared analogously.

TABLE 6

Examples of starting substances of the general formula (Vi)

(Vi)

| Ex. No. | Radical A | R¹ | B | Configuration on* C-1 | C-2 | Physical data[a] |
|---|---|---|---|---|---|---|
| V-2 | —Z | —H | —O-t-C₄H₉ | — | D | 295 (22)[b] |
| V-3 | —Z | —H | —O-t-C₄H₉ | — | L | |
| V-4 | —Z | —H | —OH | — | D | 295 (M⁺, 10) |
| V-5 | —Z | —H | —OH | — | L | |
| V-6 | —Z | —CH₃ | —O-t-C₄H₉ | L | D | 309 (16)[b] |
| V-7 | —Bn | —CH₃ | —O-t-C₄H₉ | L | L | 321 (M⁺, 1) |
| V-8 | —Bn | —CH₃ | —O-t-C₄H₉ | D | D | |
| V-9 | —Bn | —CH₃ | —O-t-C₄H₉ | D | L | |
| V-10 | —Z | —CH₃ | —OH | L | D | 309 (M⁺, 6) |
| V-11 | —Bn | —CH₃ | —OH | L | D | 265 (M⁺, 2) |
| V-12 | —Bn | —CH₃ | —OH | L | L | |
| V-13 | —Bn | —CH₃ | —OH | D | D | |
| V-14 | —Bn | —CH₃ | —OH | D | L | |
| V-15 | —Z | —C₂H₅ | —O-t-C₄H₉ | L | D | 379 (M⁺, 0.5) |
| V-16 | —Z | —C₂H₅ | —OH | L | D | 523 (M⁺, 11) |
| V-17 | —Bn | -i-C₃H₇ | —O-t-C₄H₉ | L | D | 250 (M⁺, 7) |
| V-18 | —Bn | -i-C₃H₇ | —OH | L | D | 293 (M⁺, 4) |
| V-19 | —Bn | -n-C₃H₇ | —O-t-C₄H₉ | L | D | 1.49 (—CMe₃); 2.32 (—NMe) |
| V-20 | —Bn | -n-C₃H₇ | —OH | L | D | 239 (M⁺, 1) |
| V-21 | —Bn | -i-C₄H₉ | —O-t-C₄H₉ | L | D | 363 (M⁺, 1) |
| V-22 | —Bn | -i-C₄H₉ | —OH | L | D | 307 (M⁺, 7) |
| V-23 | —Bn | -s-C₄H₉ | —O-t-C₄H₉ | L | D | 1.49 (—CMe₃); 2.26 (—NMe) |
| V-24 | —Bn | -s-C₄H₉ | —O-t-C₄H₉ | L | L | |
| V-25 | —Bn | -s-C₄H₉ | —O-t-C₄H₉ | D | D | |
| V-26 | —Bn | -s-C₄H₉ | —O-t-C₄H₉ | D | L | |
| V-27 | —Bn | -s-C₄H₉ | —OH | L | D | 307 (M⁺, 3) |
| V-28 | —Bn | -s-C₄H₉ | —OH | L | L | |
| V-29 | —Bn | -s-C₄H₉ | —OH | D | D | |
| V-30 | —Bn | -s-C₄H₉ | —OH | D | L | |

[a] FAB- or EI-MS m/z (%) or ¹H-NMR (400 MHZ, CDCl₃, δ) in ppm; in each case singlets
[b] M⁺ —CH₂=CMe₂; Z: —CO—O—CH₂-phenyl; Bn: —CH₂-phenyl

TABLE 7

Examples of compounds of the general formula (VI)

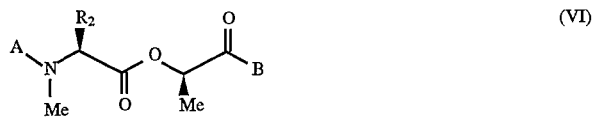

(VI)

| Ex. No. | Radical A | R² | B | Configuration on* C-3 | C-4 | Physical data[a] |
|---|---|---|---|---|---|---|
| VI-2 | —Bn | —CH₃ | —O-t-C₄H₉ | L | D | 321 (M⁺, 1) |
| VI-3 | —Bn | —CH₃ | —O-t-C₄H₉ | L | L | |
| VI-4 | —Bn | —CH₃ | —O-t-C₄H₉ | D | D | |
| VI-5 | —Bn | —CH₃ | —O-t-C₄H₉ | D | L | |
| VI-6 | —Bn | —CH₃ | —OH | L | D | 265 (M⁺, 2) |
| VI-7 | —Bn | —CH₃ | —OH | L | L | |
| VI-8 | —Bn | —CH₃ | —OH | D | D | |
| VI-9 | —Bn | —CH₃ | —OH | D | L | |
| VI-10 | —Z | -s-C₄H₉ | —O-t-C₄H₉ | L | D | 407 (M⁺, 7) |
| VI-11 | —Bn | -s-C₄H₉ | —O-t-C₄H₉ | L | D | 1.49 (—CMe₃); 2.26 (—NMe) |
| VI-12 | —Bn | -s-C₄H₉ | —O-t-C₄H₉ | L | L | |
| VI-13 | —Bn | -s-C₄H₉ | —O-t-C₄H₉ | D | D | |
| VI-14 | —Bn | -s-C₄H₉ | —O-t-C₄H₉ | D | L | |
| VI-15 | —Bn | -s-C₄H₉ | —OH | L | L | 307 (M⁺, 3) |
| VI-16 | —Bn | -s-C₄H₉ | —OH | D | D | |
| VI-17 | —Bn | -s-C₄H₉ | —OH | D | L | |

[a]FAB- or EI-MS m/z (%) or ¹H-NMR (400 MHz, CDCl₃, δ) in ppm; in each case singlets
Z: —CO—O—CH₂-phenyl; Bn: —CH₂-phenyl

TABLE 8

Examples of compounds of the general formula (VIIi)

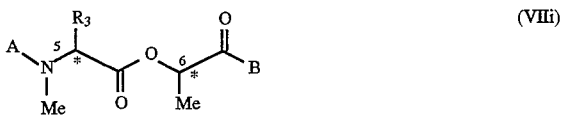

(VIIi)

| Ex. No. | Radical A | R³ | B | Configuration on* C-5 | C-6 | Physical data[a] |
|---|---|---|---|---|---|---|
| VII-2 | —H | —CH₃ | —O-t-C₄H₉ | L | D | 1.47 (—CMe₃); 2.44 (—NMe) |
| VII-3 | —H | —CH₃ | —O-t-C₄H₉ | L | L | |
| VII-4 | —H | —CH₃ | —O-t-C₄H₉ | D | D | |
| VII-5 | —H | —CH₃ | —O-t-C₄H₉ | D | L | |
| VII-6 | —H | -s-C₄H₉ | —O-t-C₄H₉ | L | L | 1.47 (—CMe₃); 2.40 |
| VII-7 | —H | -s-C₄H₉ | —O-t-C₄H₉ | D | D | (—NMe) |
| VII-8 | —H | -s-C₄H₉ | —O-t-C₄H₉ | D | L | |

[a] ¹H-NMR (400 MHz, CDCl₃, δ) in ppm; in each case singlets

We claim:
1. A cyclic depsipeptide having 18 ring atoms of the formula

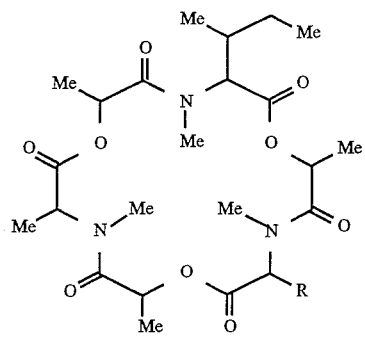 (I)

in which
R represents hydrogen, straight-chain or branched or cyclic alkyl having up to 8 carbon atoms
or its optical isomer or racemate thereof.

2. A process for the preparation of the cyclic depsipeptides according to claim 1, which comprises subjecting reacting an open-chain hexadepsipeptide of the formula

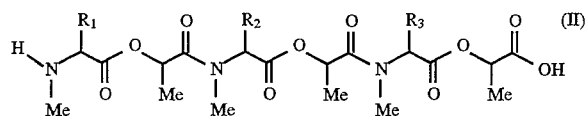 (II)

in which
one of the radicals $R^1$, $R^2$, and $R^3$ represents hydrogen, straight-chain or branched or cyclic alkyl having up to 8 carbon atoms and the two other radicals represent methyl and sec-butyl, to a cyclization reaction in the presence of a coupling reagent, in the presence of a basic reaction auxiliary and in the presence of a diluent.

3. A process for the preparation of an endoparasiticidal composition, characterized in that a cyclic depsipeptide of formula (I) according to claim 1, is mixed with at least one extender or surfactant.

4. An endoparasiticidal composition which comprises an endoparasiticidally effective amount of a cyclic depsipeptide according to claim 1, and an adjuvant.

5. A method of combatting pathogenic endoparasites in a human or animal which comprises administering an endoparasiticidally effective amount of a cyclic depsipeptide according to claim 1 to a human or animal in need thereof.

* * * * *